United States Patent [19]
Garvey et al.

[11] Patent Number: 5,874,437

[45] Date of Patent: Feb. 23, 1999

[54] NITROSATED AND NITROSYLATED PHOSPHODIESTERASE INHIBITOR COMPOUNDS, COMPOSITIONS AND THEIR USES

[75] Inventors: David S. Garvey, Dover, Mass.; Inigo Saenz de Tejada, Madrid, Spain

[73] Assignee: NitroMed, Inc., Bedford, Mass.

[21] Appl. No.: 740,764

[22] Filed: Nov. 1, 1996

[51] Int. Cl.$^6$ .................. C07D 487/04; A61K 31/445
[52] U.S. Cl. ............................. 514/258; 544/256
[58] Field of Search ............... 514/258; 544/256

[56] References Cited

U.S. PATENT DOCUMENTS

| | | | |
|---|---|---|---|
| 4,308,278 | 12/1981 | Schneider et al. | 424/273 |
| 5,196,426 | 3/1993 | Saccomano et al. | 514/258 |
| 5,223,504 | 6/1993 | Noverola et al. | 514/263 |
| 5,254,575 | 10/1993 | Pick et al. | 514/365 |
| 5,340,827 | 8/1994 | Beeley et al. | 514/352 |
| 5,426,107 | 6/1995 | Bell et al. | 514/234.2 |
| 5,491,147 | 2/1996 | Boyd et al. | 514/247 |
| 5,545,647 | 8/1996 | Tanaka et al. | 514/343 |

FOREIGN PATENT DOCUMENTS

WO 95/01338   1/1995   WIPO .

Primary Examiner—Mukund J. Shah
Assistant Examiner—Deepak R. Rao
Attorney, Agent, or Firm—Elliot M. Olstein; Raina Semionow

[57] ABSTRACT

Disclosed are nitrosated and/or nitrosylated phosphodiesterase inhibitors having the formula $NO_n$-PDE inhibitor wherein n is 1 or 2. The phosphodiesterase inhibitor can be nitrosylated or nitrosated through sites such as oxygen (hydroxyl condensation), sulfur (sulfhydryl condensation), carbon and nitrogen. The invention also provides compositions comprising such compounds in a pharmaceutically acceptable carrier. The invention also provides a composition comprising a therapeutically effective amount of an phosphodiesterase inhibitor (PDE inhibitor), which can optionally be substituted with at least one NO or $NO_2$ moiety, and one to ten fold molar excess of a compound that donates, transfers or releases nitrogen monoxide as a charged species, i.e., nitrosonium ($NO^+$) or nitroxyl ($NO^-$), or as the neutral species, nitric oxide (NO•) or which stimulates endo genous EDRF production The invention also provides compositions comprising such compounds in a pharmaceutically acceptable carrier. The invention also provides a method for treating male impotence in humans by administering the compounds and compositions thereof.

4 Claims, 30 Drawing Sheets

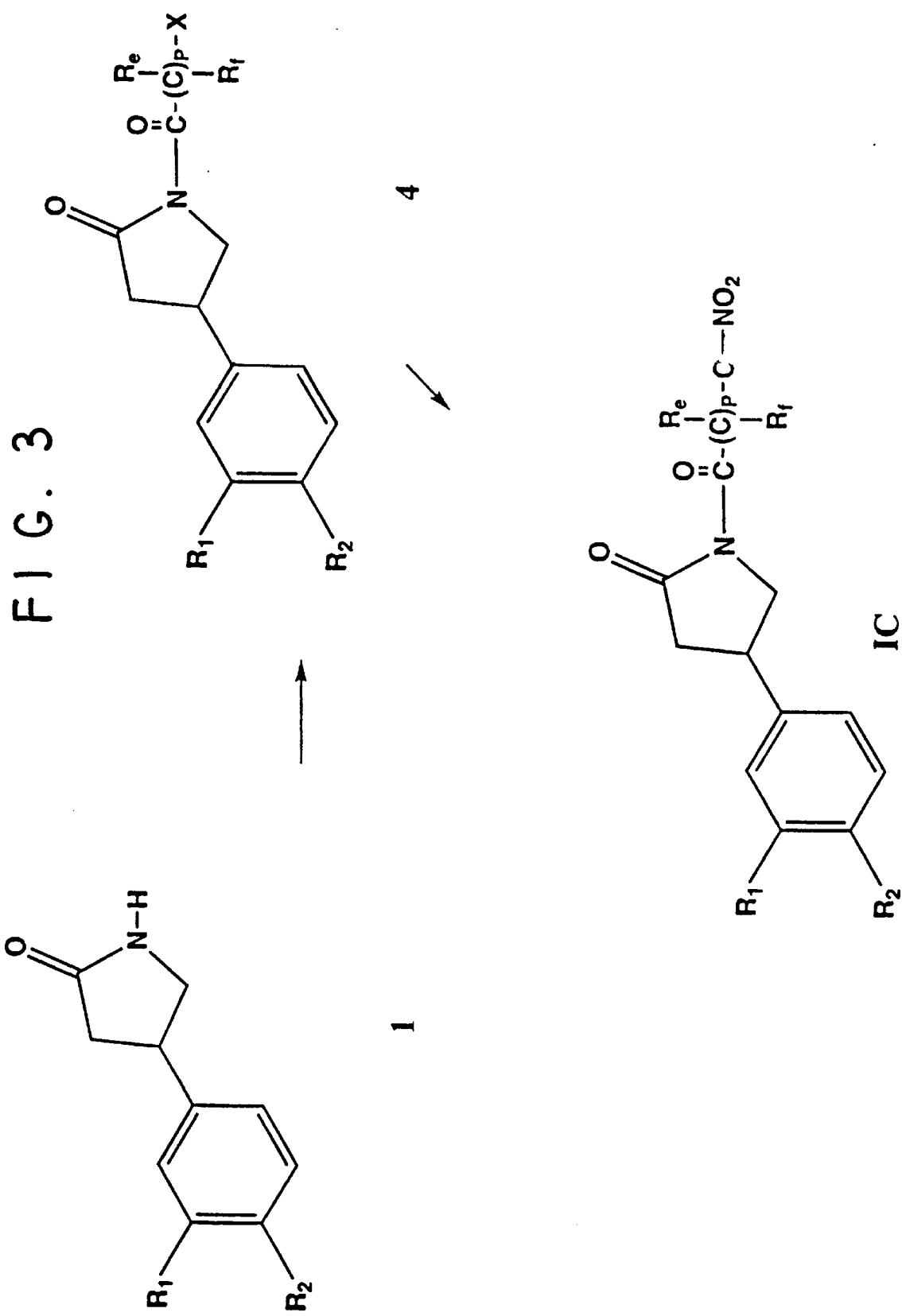
F I G. 3

FIG. 11
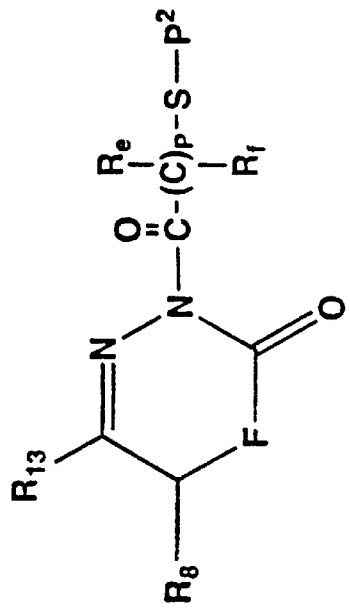
13
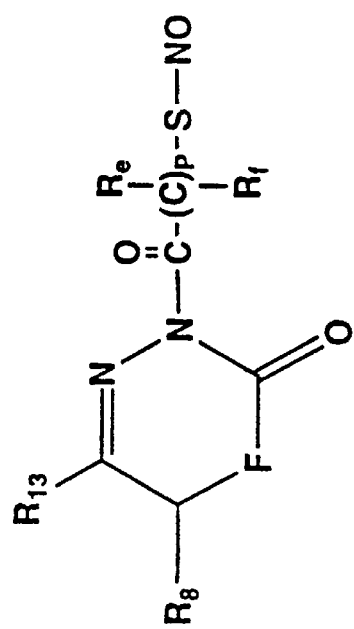
IVB
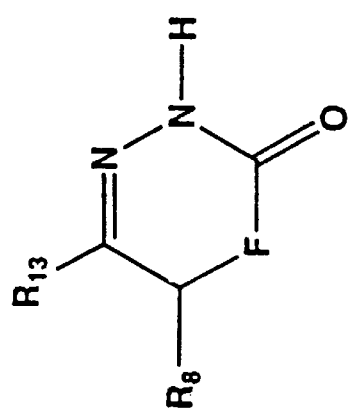
15

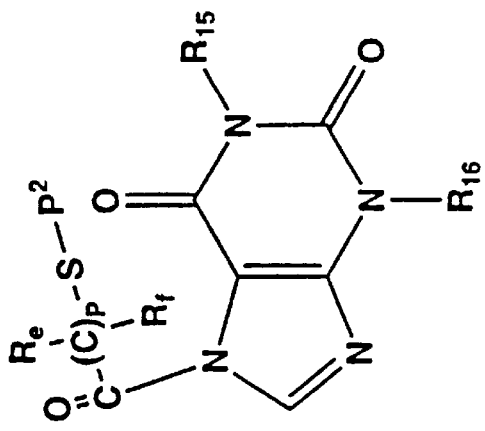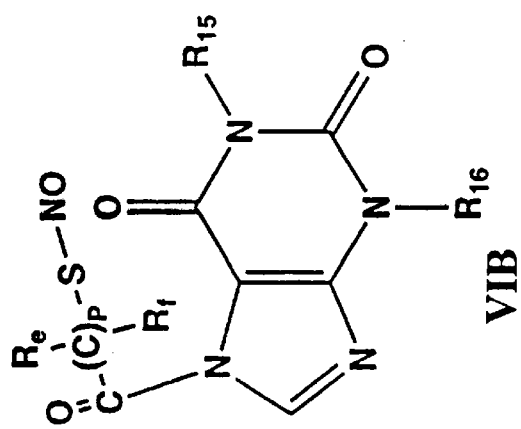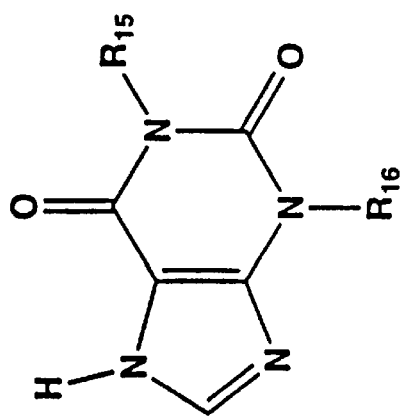
FIG. 17

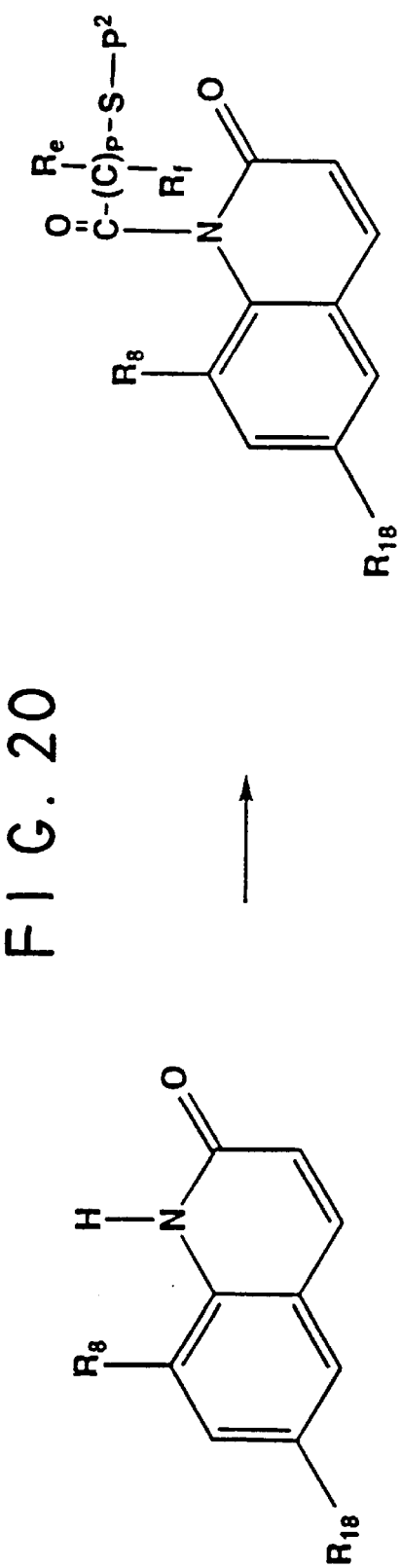
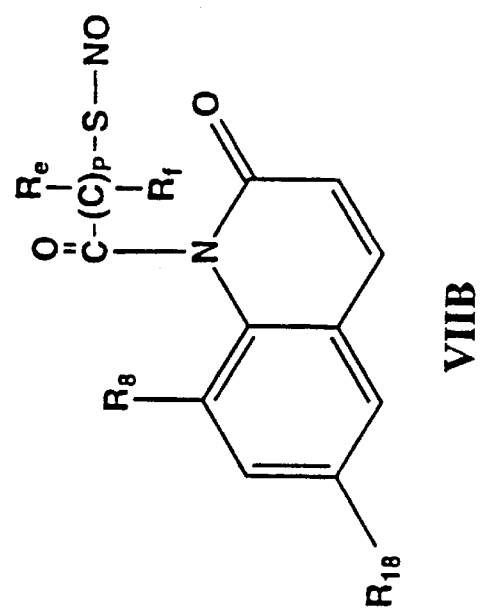
F I G. 20

F I G. 21
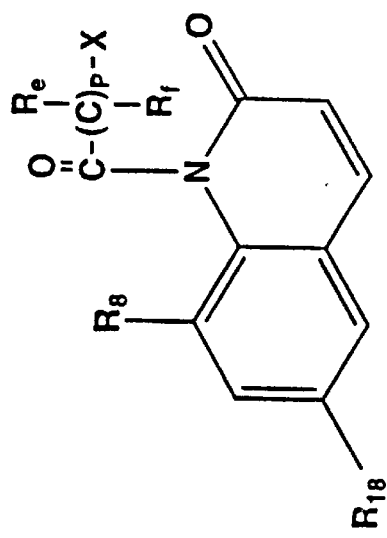
28
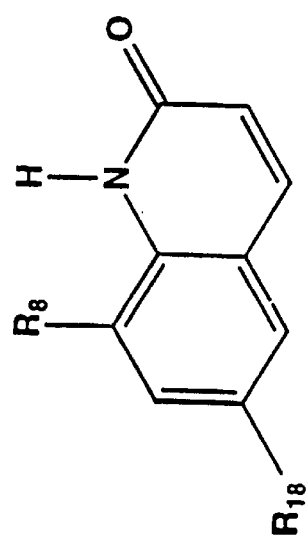
25
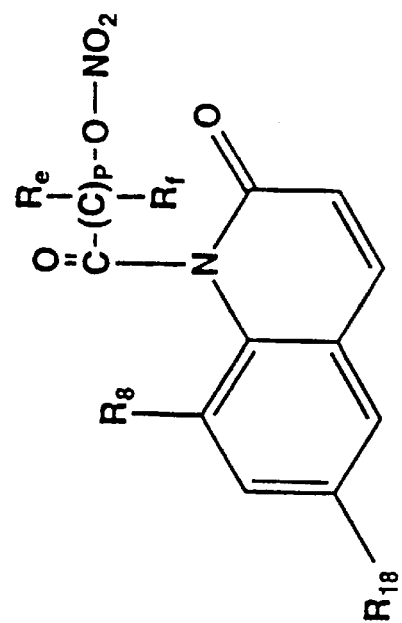
VIIC

NITROSATED AND NITROSYLATED PHOSPHODIESTERASE INHIBITOR COMPOUNDS, COMPOSITIONS AND THEIR USES

BACKGROUND OF THE INVENTION

This invention generally relates to pharmaceuticals and more specifically to a method and compositions for inducing penile erections in human males suffering from impotence.

Erectile dysfunction is a widespread disorder that is thought to affect about ten to fifteen percent of adult men. A number of causes of erectile insufficiency, in addition to anatomical deficiencies of the penis or scrotum that preclude an erection sufficient for vaginal penetration, have been identified. Causes of erectile dysfunction can be categorized as psychogenic, neurogenic, endocrinologic, drug-induced, or vasculogenic and in any individual suffering from erectile dysfunction there may be more than one cause.

Psychogenic impotence is often the result of anxiety or depression, with no apparent somatic or organic impairment. Neurogenic impotence may arise from, for example, surgery or a pelvic injury, involving the nervous system affecting the penis. Erectile dysfunction which in endocrinologic in origin is most often associated with the disorders hypo- or hyper-gonadotropic hypogonadism and hyperprolactinemia.

Vasculogenic impotence is thought to be the most frequent cause impotence accounting for approximately fifty percent of all cases of organic impotence. In these cases, the erectile dysfunction may be attributed to alterations in the flow of blood to and from the penis. Atherosclerotic or traumatic arterial occlusive disease to the arteries which supply blood to the penis can lead to a decrease in the rigidity of the erect penis as well as increase the time to achieving maximal erection. In still other cases, there is leakage from veins in the penis such that sufficient pressure for an erection can be neither obtained nor maintained.

There is also a high incidence of erectile insufficiency among diabetics, particularly those with insulin-dependent diabetes mellitus. Erectile dysfunction in diabetics is often classified as "diabetogenic," although the underlying dysfunction is usually neurogenic, but may be vasculogenic or neurogenic and vasculogenic. About half of diabetic males suffer from erectile insufficiency, and about half of the cases of neurogenic impotence are in diabetics.

Erectile insufficiency is sometimes a side effect of certain drugs, such as beta-antagonists that are administered to reduce blood pressure in persons suffering from hypertension, or drugs administered to treat depression or anxiety. Excessive alcohol consumption has also been linked to erectile insufficiency. These forms of erectile insufficiency may be regarded as a subset of neurogenic or psychogenic insufficiency.

A number of methods to treat impotence are available. These treatments include pharmacological treatments, surgery and, in cases of psychogenic dysfunction, psychological counseling is sometimes effective. Psychogenic impotence often can be cured by counseling coupled with a demonstration to the patient that he is capable of having a full erection by inducing such an erection from one to a few times in the patients. Insufficiency due to excessive alcohol consumption is sometimes cured by reducing or elimination such consumption.

In the rare cases, where the insufficiency is untreatable because of venous leakage, surgery can usually be employed to repair the venous lesion and thereby either cure the insufficiency or, if there remains an erectile insufficiency after repair of the venous lesion, render the insufficiency amenable to treatment by pharmacological methods. Also, penile implants, which provide a mechanic means to produce an erection sufficient for vaginal penetration, are widely used to treat impotence. In recent years, implants have been employed, especially in cases where pharmacological intervention is ineffective, which are usually cases of severe vasculogenic impotence. Treatment of impotence with penile implants, however, entails serious disadvantages. Such treatment requires surgery and necessitates total destruction of the erectile tissues of the penis, forever precluding normal erection.

Pharmacological methods of treatment are also available. Such methods, however, have not proven to be highly satisfactory or without potentially severe side-effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a phosphodiesterase inhibitor and a smooth muscle relaxant, or phenoxybenzamine, a non-specific antagonist and hypotensive, into a corpus cavernosum has been found to cause an erection sufficient for vaginal penetration however, these treatments are not without the serious and often painful side effect of priapisim. Also, in cases where severe atherosclerosis is not a cause of the dysfunction, intracavernosal injection of phentolamine, an $\alpha$-adrenergic antagonist, causes an erection sufficient for vaginal penetration. The resulting erection is one of significantly shorter duration than that induced by intracavernosal injection of papaverine or phenoxybenzamine and often times is of such short duration that satisfactory sexual relations are difficult or impossible. As an alternative or, in some cases an adjunct to phosphodiesterase inibition or $\alpha$-adrenergic blockade for the treatment of erectile dysfunction, prostaglandin E1 (PGE1) has been administered via intracavernosal injection. A major side effect frequently associated intracorprally delivered PGE1 is penile pain and burning. Thus, there is a need for methods to induce and maintain a penile erection for a sufficient duration that satisfactory sexual relations are possible without also producing the undesirable side effects of those agents currently used.

Nitric oxide (NO) has been shown to mediate a number of actions including the bactericidal and tumoricidal actions of macrophages and blood vessel relaxation of endothelial cells. NO, and NO donors have also been implicated as mediators of nonvascular smooth muscle relaxation. This effect includes the dilation of the corpus cavernosum smooth muscle, an event involved in the penile erection process. However, the effects of modified of phosphodiesterase inhibitors which are directly or indirectly linked with a nitric oxide adduct have not been investigated.

SUMMARY OF THE INVENTION

In the process of arriving at the present invention it was recognized that the risk of toxicities and adverse effects that are associated with high doses of phosphodiesterase inhibitors can be avoided by the use of such phosphodiesterase inhibitors when nitrosated or nitrosylated. Such toxicities and adverse effects include hypotension, syncope, as well as priapism. The smooth muscle relaxant properties of phosphodiesterase inhibitors and of compounds that donate, release or transfer nitrogen monoxide work together to permit the same efficacy with lower doses of the phosphodiesterase inhibitors.

Accordingly, in one aspect the invention provides novel nitrosated and nitrosylated phosphodiesterase inhibitors ($NO_n$-PDE inhibitor) wherein n is 1 or 2. The phosphodiesterase inhibitor can be nitrosylated or nitrosated through sites such as oxygen (hydroxyl condensation), sulfur (sulfhydryl condensation), carbon and nitrogen. The invention also provides compositions comprising such compounds in a pharmaceutically acceptable carrier.

In another aspect the invention provides a composition comprising a therapeutically effective amount of an phosphodiesterase inhibitor (PDE inhibitor), which can optionally be substituted with at least one NO or $NO_2$ moiety, and one to ten fold molar excess of a compound that donates, transfers or releases nitrogen monoxide as a charged species, i.e., nitrosonium ($NO^+$) or nitroxyl ($NO^-$), or as the neutral species, nitric oxide (NO•). The invention also provides compositions comprising such compounds in a pharmaceutically acceptable carrier.

In another aspect, the invention provides a method for treating male impotence in humans which comprises administering to an individual in need thereof a therapeutically effective amount of a nitrosated or nitrosylated PDE inhibitor.

In another aspect, the invention provides a method for treating male impotence in humans which comprises administering to an individual in need thereof a composition comprising a therapeutically effective amount of an PDE inhibitor which can optionally be substituted with at least one NO or $NO_2$ moiety, and a compound that donates, transfers or releases nitric oxide as a charged species, i.e., nitrosonium ($NO^+$) or nitroxyl ($NO^-$), or as the neutral species, nitric oxide (NO•). The PDE inhibitor or PDE inhibitor directly or indirectly linked to at least one NO or $NO_2$ group, and nitric oxide donor can be administered separately or as components of the same composition.

The nitrosated or nitrosylated PDE inhibitor and the compound that donates, transfers or releases nitric oxide and/or stimulates endogenous production of NO or EDRF in vivo can be administered separately or as components of the same composition in one or more pharmaceutically acceptable carriers.

The following drawings are illustrative of embodiments of the invention and do not limit the scope of the invention as defined by the claims.

BRIEF DESCRIPTION OF THE DRAWINGS

FIG. 3 Synthetic scheme for the preparation of nitrate containing substituted benzene derivatives.

FIG. 11 Synthetic scheme for the preparation of nitrosothiol containing pyrimidin-4-one derivatives.

FIG. 17 Synthetic scheme for the preparation of nitrosothiol containing purine-2,6-dione derivatives.

FIG. 20 Synthetic scheme for the preparation of nitrosothiol containing quinoline derivatives.

FIG. 21 Synthetic scheme for the preparation of nitrate containing quinoline derivatives.

Figure 1:
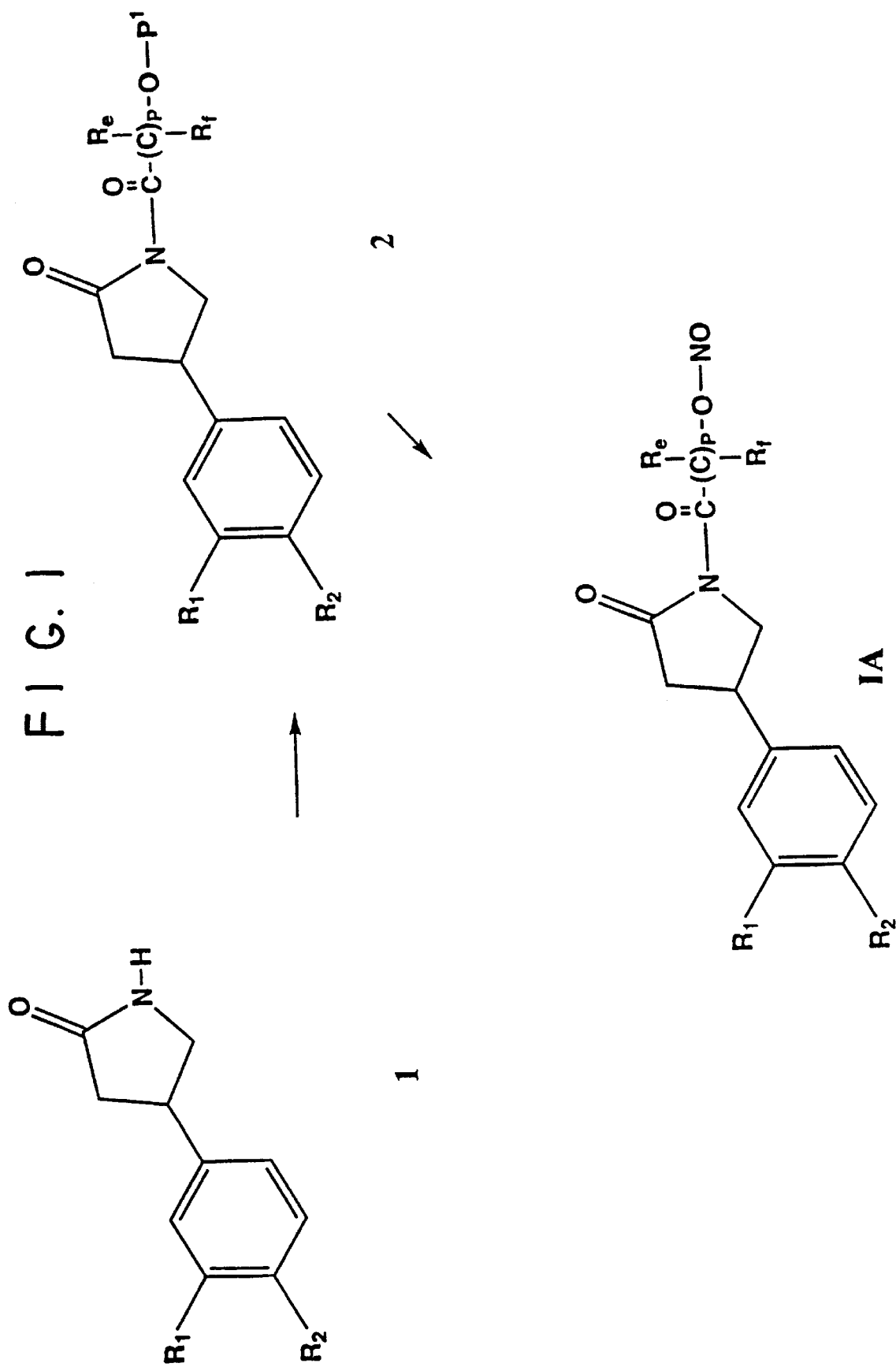
FIG. 1 Synthetic scheme for the preparation of nitrite containing substituted benzene derivatives.

The term "lower alkyl" as used herein refers to branched or straight chain alkyl groups comprising one to ten carbon atoms, including methyl, ethyl, propyl, isopropyl, n-butyl, t-butyl, neopentyl and the like.

The term "alkoxy" as used herein refers to $R_{50}O-$ wherein $R_{50}$ is lower alkyl as defined in this specification. Representative examples of alkoxy groups include methoxy, ethoxy, t-butoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "hydroxy" as used herein refers to —OH.

The term "hydroxyalkyl" as used herein refers to a hydroxy group as previously defined appended to a lower alkyl group as previously defined.

The term "alkenyl" as used herein refers to a branched or straight chain $C_2$–$C_{10}$ hydrocarbon which also comprises one or more carbon-carbon double bonds.

The term "amino" as used herein refers to —$NH_2$.

The term "nitrate" as used herein refers to —O—$NO_2$.

The term "alkylamino" as used herein refers to $R_{50}$NH- wherein $R_{50}$ is as defined in this specification, for example, methylamino, ethylamino, butylamino, and the like.

The term "dialkylamino" as used herein refers to $R_{52}R_{53}$N- wherein $R_{52}$ and $R_{53}$ are independently selected from lower alkyl groups as defined in this specification, for example dimethylamino, diethylamino, methyl propylamino and the like.

The term "nitro" as used herein refers to the group —$NO_2$ and "nitrosated" refers to compounds that have been substituted therewith.

The term "nitroso" as used herein refers to the group —NO and "nitrosylated" refers to compounds that have been substituted therewith.

The term "aryl" as used herein refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from lower alkyl, haloalkyl, alkoxy, amino, alkylamino, dialkylamino, hydroxy, halo, and nitro. In addition, substituted aryl groups include tetrafluorophenyl and pentafluorophenyl.

The term "alkylaryl" as used herein refers to a lower alkyl radical to which is appended an aryl group. Representative arylalkyl groups include benzyl, phenylethyl, hydroxybenzyl, fluorobenzyl, fluorophenylethyl and the like.

The term "arylalkoxy" as used herein refers to an alkoxy radical to which is appended an aryl group. Representative arylalkoxy groups include benzyloxy, phenylethoxy, chlorophenylethoxy and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "bridged cycloalkyl" herein refers to two or more cycloalkyl radicals fused via adjacent or non-adjacent carbon atoms, including but not limited to adamantyl and decahydronapthyl.

The term "cycloalkoxy" as used herein refers to $R_{54}$O— wherein $R_{54}$ is cycloalkyl as defined in this specification. Representative examples of alkoxy groups include cyclopropoxy, cyclopentyloxy, and cyclohexyloxy and the like.

The term "arylthio" herein refers to $R_{55}$S— wherein $R_{55}$ is an aryl group.

The term "alkylsulfinyl" herein refers to $R_{50}$—S(O)$_2$— wherein $R_{50}$ is as defined in this specification.

The term "carboxamido" herein refers to —C(O)$NH_2$.

The term "carbamoyl" herein refers to —O—C(O)$NH_2$.

The term "carboxyl" herein refers to —$CO_2$H.

The term "carbonyl" herein refers to —C(O)—.

The term "halogen" or "halo" as used herein refers to I, Br, Cl, or F.

The term "haloalkyl" as used herein refers to a lower alkyl radical to which is appended one or more halogens. Representative examples of a haloalkyl group include trifluoromethyl, chloromethyl, 2-bromobutyl, 1-bromo-2-chloro-pentyl and the like.

The term "haloalkoxy" as used herein refers to a haloalkyl radical to which is appended an alkoxy group. Representative examples of haloalkoxy groups include, 1,1,1-trichloroethoxy, 2-bromobutoxy and the like.

The term "heteroaryl" as used herein refers to a mono- or bi- cyclic ring system containing one or two aromatic rings and containing at least one nitrogen, oxygen, or sulfur atom in an aromatic ring. Heteroaryl groups (including bicyclic heteroaryl groups) can be unsubstituted or substituted with one, two or three substituents independently selected from lower alkyl, haloalkyl, alkoxy, amino, alkylamino, dialkylamino, hydroxy, halo and nitro. Examples of heteroaryl groups include but are not limited to pyridine, pyrazine, pyrimidine, pyridazine, pyrazole, triazole, thiazole, isothiazole, benzothiazole, benzoxazole, thiadiazole, oxazole, pyrrole, imidazole and isoxazole.

The term "heterocyclic ring" refers to any 3-, 4-, 5-, 6-, or 7-membered nonaromatic ring containing at least one nitrogen atom, oxygen, or sulfur atom which is bonded to an atom which is not part of the heterocyclic ring.

The term "arylheterocyclic ring" as used herein refers to a bi- or tricyclic ring comprised of an aryl ring as previously defined appended via two adjacent carbons of the aryl group to a heterocyclic ring as previously defined.

The term "heterocyclic compounds" herein refers to mono and polycyclic compounds containing at least one heteroaryl or heterocyclic ring.

The term "amido" as used herein refers to —NH—C(O)—$R_{56}$ wherein $R_{56}$ is a lower alkyl, aryl, or hereroaryl group as defined in this specification The term "alkylamido" as used herein refers to $R_{50}$N—C(O)—$R_{56}$ wherein $R_{50}$ is as defined in this specification and $R_{56}$ is a lower aryl, aryl, or hereroaryl group as defined in this specification.

Examples of contemplated PDE inhibitors include dipyridamole, zaprinast, sildenafil, filaminast, denbufyllene, piclamilast, zardaverine, and rolipram.

Sources of information for the above include Goodman and Gilman, The Pharmacological Basis of Therapeutics (9th Ed.), McGraw-Hill, Inc., 1996; the Physician's Desk Reference (49th Ed.), Medical Economics (1995); Drug Facts and Comparisons (1993 Ed), Facts and Comparisons (1993); and The Merck Index (12th Ed.), Merck & Co., Inc. (1996), all of which are incorporated herein by reference in their entirety.

A principal aspect of the invention relates to novel nitrosated and/or nitrosylated phosphodiesterase inhibitors.

One embodiment of this aspect provides compounds having the structure:

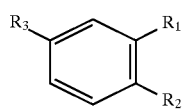

I wherein, $R_1$ is alkoxy, cycloalkoxy, halogen, or

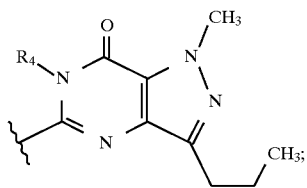

$R_2$ is hydrogen, alkoxy, or haloalkoxy; and $R_3$ is selected from:

(i) 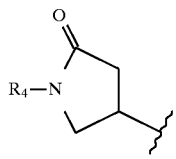

(ii) 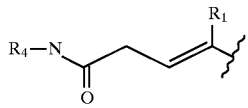

(iii) 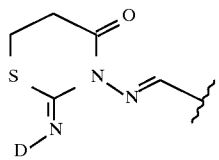

(iv) 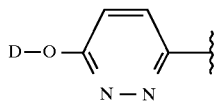

(v) 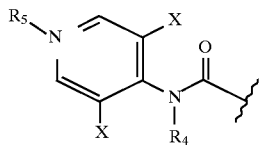

(vi) 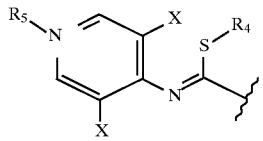

(vii) 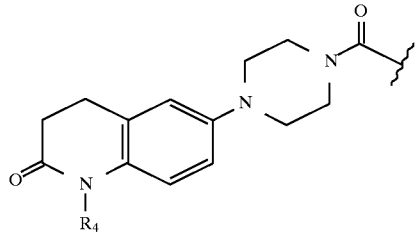

(viii) 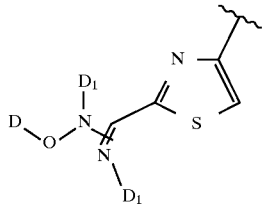

(ix) 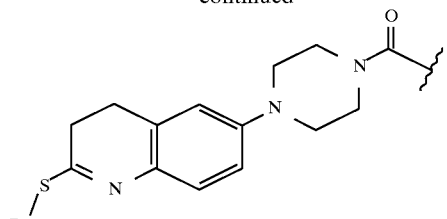

(x) 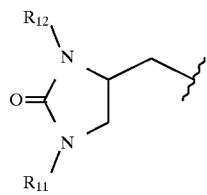

wherein

D is selected from (i) —NO; (ii) —NO$_2$; (iii) —C(R$_d$)—O—C(O)—Y—Z—[C(R$_e$)(R$_f$)]$_p$—T—Q in which R$_d$ is hydrogen, lower alkyl, cycloalkyl, aryl, alkylaryl, aryl or heteroaryl, Y is oxygen, sulfur, carbon or NR$_i$ in which R$_i$ is hydrogen, lower alkyl, R$_e$ and R$_f$ are independently selected from hydrogen, lower alkyl, cycloalkyl, aryl, heteroaryl, arylalkyl, amino, alkylamino, amido, alkylamido, dialkylamino, carboxy, or carboxamido or taken together are carbonyl, cycloalkyl or bridged cycloalkyl, p is an integer from 1 to 6, T is a covalent bond, oxygen, sulfur or nitrogen, Z is selected from a covalent bond, alkyl, cycloalkyl, aryl, heteroaryl, arylalkyl or arylheterocyclic ring, and Q is selected from —NO or —NO$_2$; (iv) —C(O)—T$^1$—Z—[C(R$_e$)(R$_f$)]$_p$—T$^2$—Q wherein T$^1$ and T$^2$ are independently selected from T and R$_e$, R$_f$, p, Q, Z, and T are as defined in this specification; (v) —C(O)—Z—[G—[C(R$_e$)(R$_f$)]$_p$—T—Q—]$_p$ wherein G is (i) a covalent bond; (ii) —T—C(O)—; (iii) —C(O)—T, or (iv) Y, and wherein R$_e$, R$_f$, p, Q, T, Y, and Z are as defined in this specification;

R$_4$ is selected from (i) hydrogen, (ii) —C(R$_d$)—O—C(O)—Y—Z—[C(R$_e$)(R$_f$)]$_p$—T—Q, (iii) —C(O)—T$^1$—[C(R$_e$)(R$_f$)]$_p$—T$^2$—Q, (iv) —C(O)—Z—[G—[C(R$_e$)(R$_f$)]$_p$—T—Q]$_p$; and wherein R$_d$, R$_e$, R$_f$, p, G, T, T$^1$, T$^2$, Q, Y, and Z are defined as in this specification;

R$_5$ is selected from a lone pair of electrons or —C(R$_d$)—O—C(O)—Y—Z—[C(R$_e$)(R$_f$)]$_p$—T—Q wherein R$_d$, R$_e$, R$_f$, p, T, T$^1$, T$^2$, Q, Y, and Z are defined as in this specification;

R$_{11}$, and R$_{12}$ are independently selected from hydrogen or R$_4$ wherein R$_4$ is as defined in this specification with the provision that R$_{11}$ and R$_{12}$ are not both hydrogen;

X is a halogen and;

D$_1$ is selected from D or hydrogen and wherein D is as defined in this specification.

Another embodiment of this aspect provides compounds having the structure:

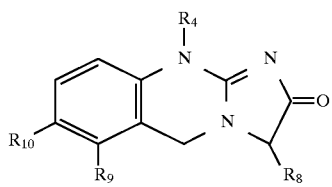

wherein, $R_4$ is as defined in this specification;
$R_8$ is selected from hydrogen or lower alkyl;
$R_9$ is selected from hydrogen or halogen; and
$R_{10}$ is selected from:

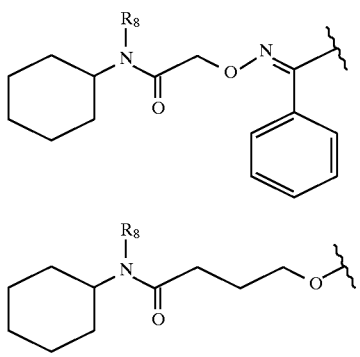

wherein $R_8$ is as defined in this specification.

Another embodiment of this aspect provides compounds having the structure:

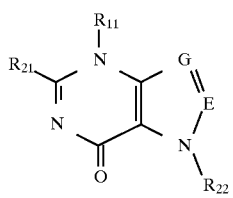

wherein,

E is selected from nitrogen or —CH—;
G is selected from nitrogen or —C($R_8$)—;
$R_{21}$, is selected from:

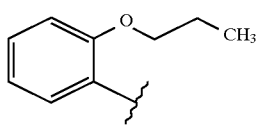

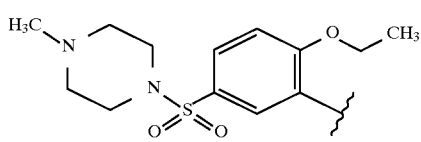

$R_{22}$ is selected from $R_{12}$ or lower alkyl; and
$R_8$, $R_{11}$, and $R_{12}$ are as defined in this specification.

Another embodiment of this aspect provides compounds having the structure:

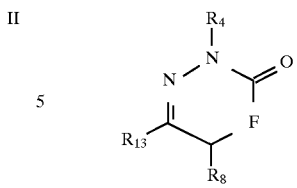

wherein,

F is selected from —CH$_2$— or sulfur;
$R_4$ and $R_8$ are as defined in this specification; and
$R_{13}$ is selected from:

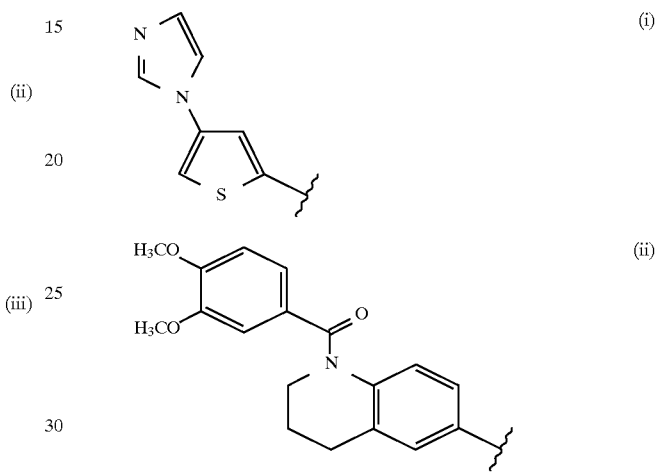

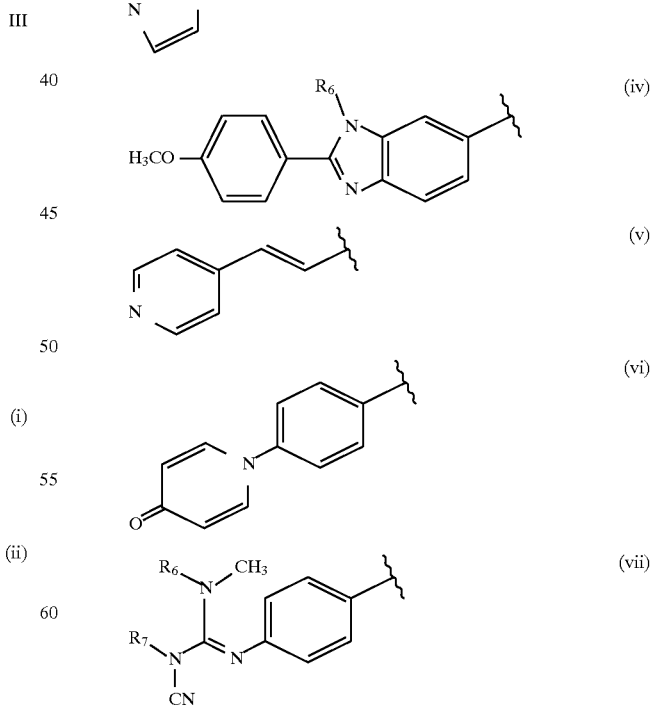

wherein, $R_6$ and $R_7$ are independently selected from hydrogen or $R_4$ wherein $R_4$ is as defined in this specification.

Another embodiment of this aspect provides compounds having the structure:

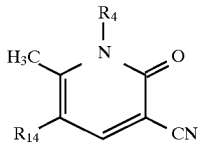
V wherein, $R_4$ is as defined in this specification; and $R_{14}$ is selected from:

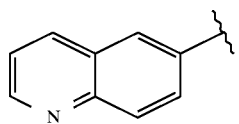
(i)

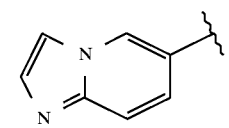
(ii)

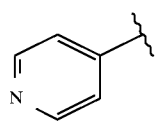
(iii)

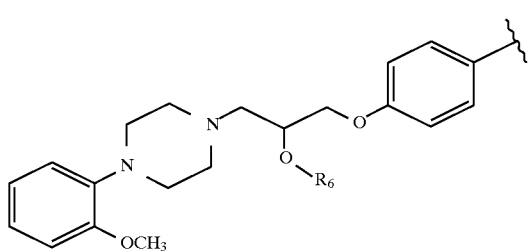
(iv)

wherein $R_6$ is as defined in this specification.

Another embodiment of this aspect provides compounds having the structure:

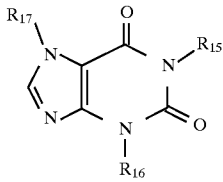
VI wherein, $R_{15}$ is hydrogen, lower alkyl, $R_4$, or —$(CH_2)_4$—$C(CH_3)_2$—O—$D_1$;

$R_{16}$ is lower alkyl; and $R_{17}$ is hydrogen, lower alkyl, $CH_3$—$C(O)$—$CH_2$—, $CH_3$—O—$CH_2$—, or D with the provision that either $R_{15}$ or $R_{17}$ must be selected to contain D and wherein D and $D_1$ are as defined in this specification.

Another embodiminent of this aspect provides compounds having the structure:

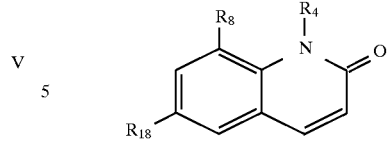
VII wherein, $R_4$ and $R_8$ are as defined in this specification and $R_{18}$ is selected from:

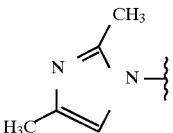
(i)

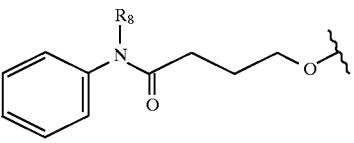
(ii)

and wherein $R_8$ is as defined in this specification.

Another embodiment of this aspect provides compounds having the structure:

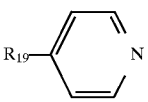
VIII wherein, $R_{19}$ is selected from:

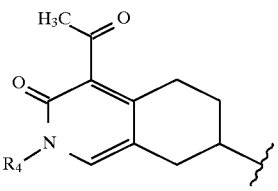
(i)

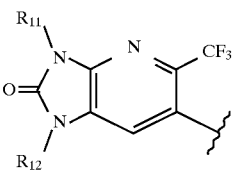
(ii)

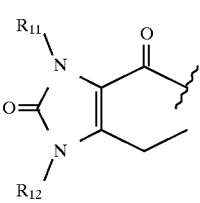
(iii)

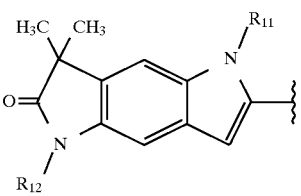
(iv)

and wherein
$R_4$, $R_{11}$, and $R_{12}$ are defined as in this specification.

Another embodiment of this aspect provides compounds having the structure:

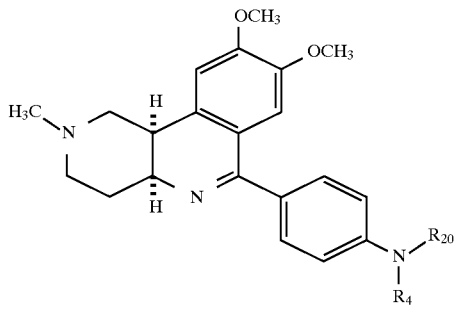

wherein,
$R_{20}$ is selected from:

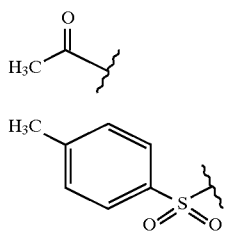

and wherein
$R_4$ is defined as in this specification.

Another embodiment of this aspect provides compounds having the structure:

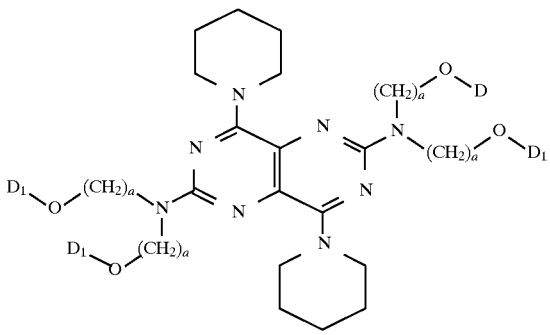

wherein,
a is an integer from 2 to 3 and D and $D_1$ are defined as in this specification.

Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another aspect of the invention provides processes for making the novel compounds of the invention and to the intermediates useful in such processes.

Some of the compounds of the invention are synthesized as shown in FIGS. 1 through 30 presented below, in which $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_e$, $R_f$, a, p, D, $D_1$, E, F, G, and X are as defined in this specification or as depicted in the reaction schemes for structures I–X; $P^1$ is an oxygen protecting group and $P^2$ is a sulfur protecting group. The reactions are performed in solvents appropriate to the reagents and materials employed are suitable for the transformations being effected. It is understood by those skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of sulfur and oxygen protecting groups is well known in the art for protecting thiol and alcohol groups against undesirable reactions during a synthetic procedure and many such protecting groups are known, c.f., T. H. Greene and P. G. M. Wuts, *Protective Groups in Organic Synthesis*, John Wiley & Sons, New York (1991).

Another embodiment of this aspect provides processes for making compounds having structures I and to the intermediates useful in such processes as follows.

Nitroso compounds of formula (I) wherein $R_1$, $R_2$, $R_e$, $R_f$, and p are defined as in this specification and a nitrite containing imide is representative of the $R_3$ group as defined in this specification may be prepared as outlined in FIG. 1. The amide group of formula 1 is converted to the imide of formula 2 wherein p, $R_e$ and $R_f$ are defined as in this specification by reaction with an appropriate protected alcohol containing activated acylating agent wherein $P^1$ is as defined in this specification. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a trimethylsilyl ether, a tert-butyldimethylsilyl ether, or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IA.

Figure 2:
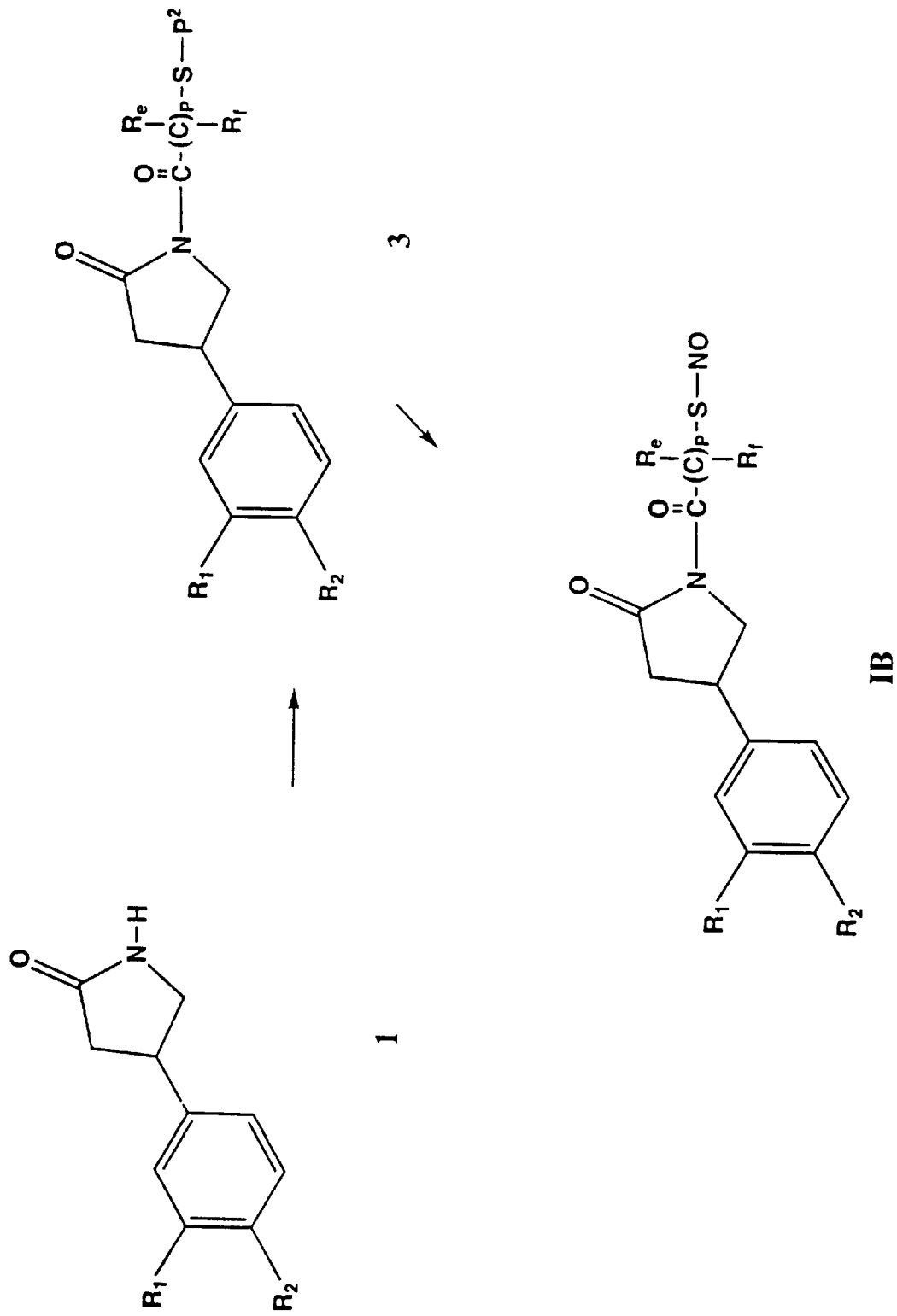
FIG. 2 Synthetic scheme for the preparation of nitrosothiol containing substituted benzene derivatives.

Nitroso compounds of formula (I) wherein $R_1$, $R_2$, $R_e$, $R_f$, and p are defined as in this specification and a nitrosothiol containing imide is representative of the $R_3$ group as defined in this specification may be prepared as outlined in FIG. 2. The amide group of formula 1 is converted to the imide of formula 3 wherein p, $R_e$ and $R_f$ are defined as in this specification by reaction with an appropriate protected thiol containing activated acylating agent wherein $P^2$ is as defined in this specification. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IB. Alternatively, treatment of the deprotected thiol derived from compound 3 with a stoichiometric quantity of sodium nitrite in an acidic aqueous or alcoholic solution affords the compound of the formula IB.

Nitro compounds of formula (I) wherein $R_1$, $R_2$, $R_e$, $R_f$, and p are defined as in this specification and an nitrate containing imide is representative of the $R_3$ group as defined in this specification may be prepared as outlined in FIG. 3. The amide group of the formula 1 is converted to the imide of the formula 4 wherein p, $R_e$ and $R_f$ are defined as in this specification and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 4 with a suitable nitrating agent such as silver nitrate in an inert solvent such as acetonitrile affords the compound of the formula IC.

Another embodiment of this aspect provides processes for making compounds having structures II and to the intermediates useful in such processes as follows.

Figure 4:
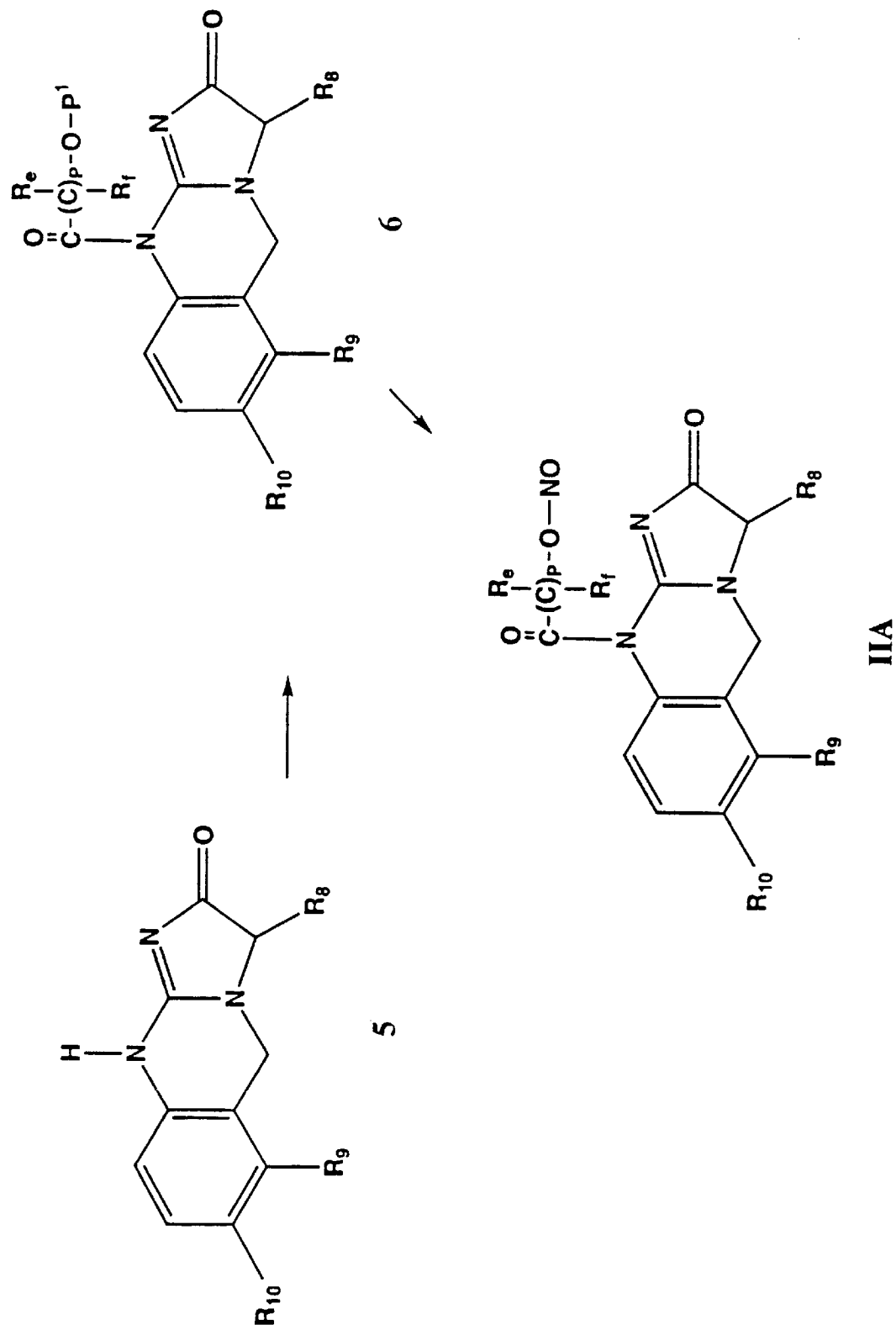
FIG. 4 Synthetic scheme for the preparation of nitrite containing imidazo [2,1-b]quinazoline derivatives.

Nitroso compounds of formula (II) wherein $R_8$, $R_9$, $R_{10}$, $R_e$, $R_f$, and p are defined as in this specification, and a nitrite containing amide is representative of the $R_4$ group as defined in this specification may be prepared as outlined in FIG. 4. The imidazo[2,1-b]quinazoline of formula 5 is converted to the acylimidazo[2,1-b]quinazoline of formula 6 wherein p, $R_e$ and $R_f$ are defined as in this specification by reaction with an appropriate protected alcohol containing activated acylating agent wherein $P^1$ is as defined in this specification. Preferred methods for the formation of acylimidazo[2,1-b]quinazolines are reacting the imidazo[2,1-b]quinazoline with the preformed acid chloride or symmetrical anhydride of the protected alcohol containing acid or condensing the imidazo[2,1-b]quinazoline and protected alcohol containing acid in the presence of a dehydrating agent such as dicyclohexylcarbodiimide (DCC) or 1-ethyl-3 (3-dimethylaminopropyl) carbodiimide hydrochloride (EDAC·HCl) with or without a catalyst such as 4-dimethylaminopyridine (DMAP) or 1-hydroxybenzotriazole (HOBt). Preferred protecting groups for the alcohol moiety are silyl ethers such as a trimethylsilyl or tertbutyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, TBF, DME, or acetonitrile with or without an amine base such as pyridine or triethylamine affords the compound of the formula IIA.

Figure 5:
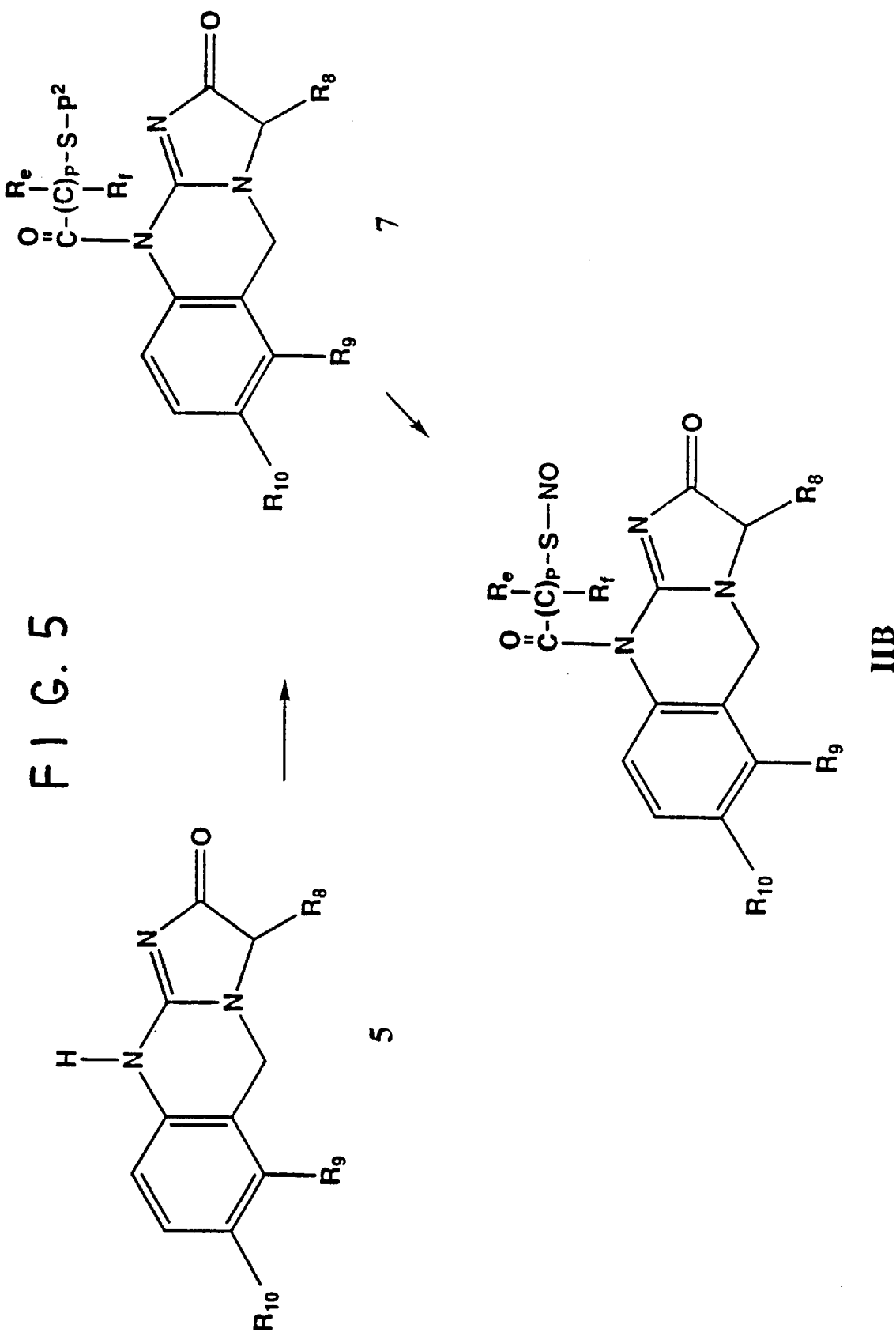
FIG. 5 Synthetic scheme for the preparation of nitrosothiol containing imidazo[2,1-b]quinazoline derivatives.

Nitroso compounds of formula (II) wherein $R_8$, $R_9$, $R_{10}$, $R_e$, $R_f$, and p are defined as in this specification, and a nitrosothiol containing amide is representative of the $R_4$ group as defined in this specification may be prepared as outlined in FIG. 5. The imidazo[2,1-b]quinazoline of formula 5 is converted to the acylirnidazo[2,1-b]quinazoline of formula 7 wherein p, $R_e$ and $R_f$ are defined as in this specification by reaction with an appropriate protected thiol containing activated acylating agent wherein $P^2$ is as defined in this specification. Preferred methods for the formation of acylated imidazo[2,1-b]quinazolines are reacting the imidazo[2,1-b]quinazoline with the preformed acid chloride or symmetrical anhydride of the protected thiol containing acid or condensing the imidazo[2,1-b]quinazoline and protected thiol containing acid in the presence of a dehydrating agent such as DCC or EDAC·HCl with or without a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IIB. Alternatively, treatment of the deprotected thiol derived from compound 7 with a stoichiometric quantity of sodium nitrite in an acidic aqueous or alcoholic solution affords the compound of the formula IIB.

Figure 6:
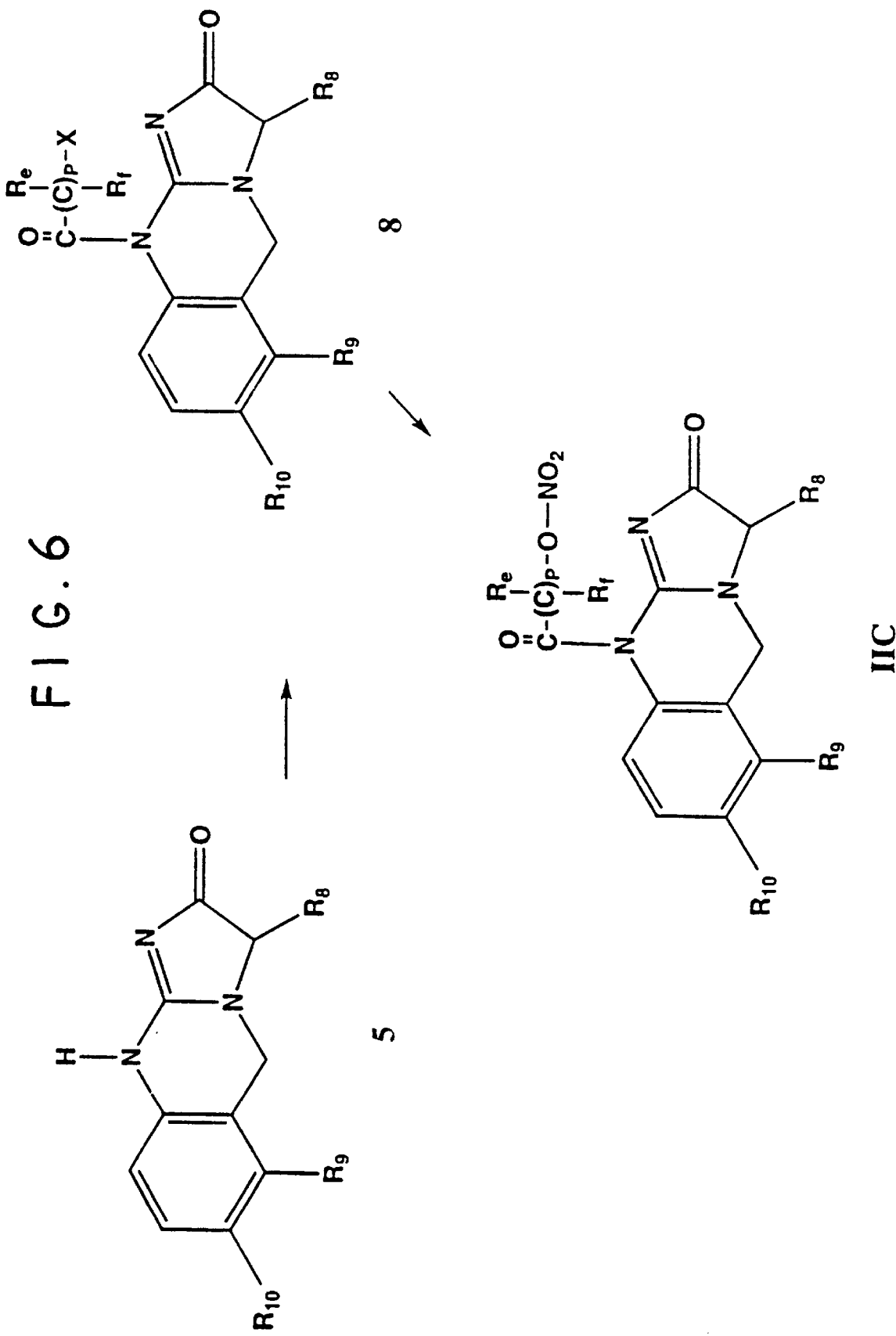
FIG. 6 Synthetic scheme for the preparation of nitrate containing imidazo[2,1-b]quinazoline derivatives.

Nitro compounds of formula (II) wherein $R_8$, $R_9$, $R_{10}$, $R_e$, $R_f$, and p are defined as in this specification, and a nitrate containing amide is representative of the $R_4$ group as defined in this specification may be prepared as outlined in FIG. 6. The imidazo[2,1-b]quinazoline of formula 5 is converted to the acylimidazo[2,1-b]quinazoline of formula 8 wherein p, $R_e$ and $R_f$ are defined as in this specification and X is a halogen by reaction with an appropriate halide containing activated acylating agent. Preferred methods for the formation of the acylimidazo[2,1-b]quinazolines are reacting the imidazo[2,1-b]quinazoline with the preformed acid chloride or symmetrical anhydride of the halide containing acid or condensing the alcohol and halide containing acid in the presence of a dehydrating agent such as DCC or EDAC·HCl with or without a catalyst such as DMAP or HOBt. Preferred halides are bromide and iodide. Reaction of the acylimidazo[2,1-b]quinazoline of the formula 8 with a suitable nitrating agent such as silver nitrate in an inert solvent such as acetonitrile affords the compound of the formula IIC.

Another embodiment of this aspect provides processes for making compounds having structures III and to the intermediates useful in such processes as follows.

Figure 7:
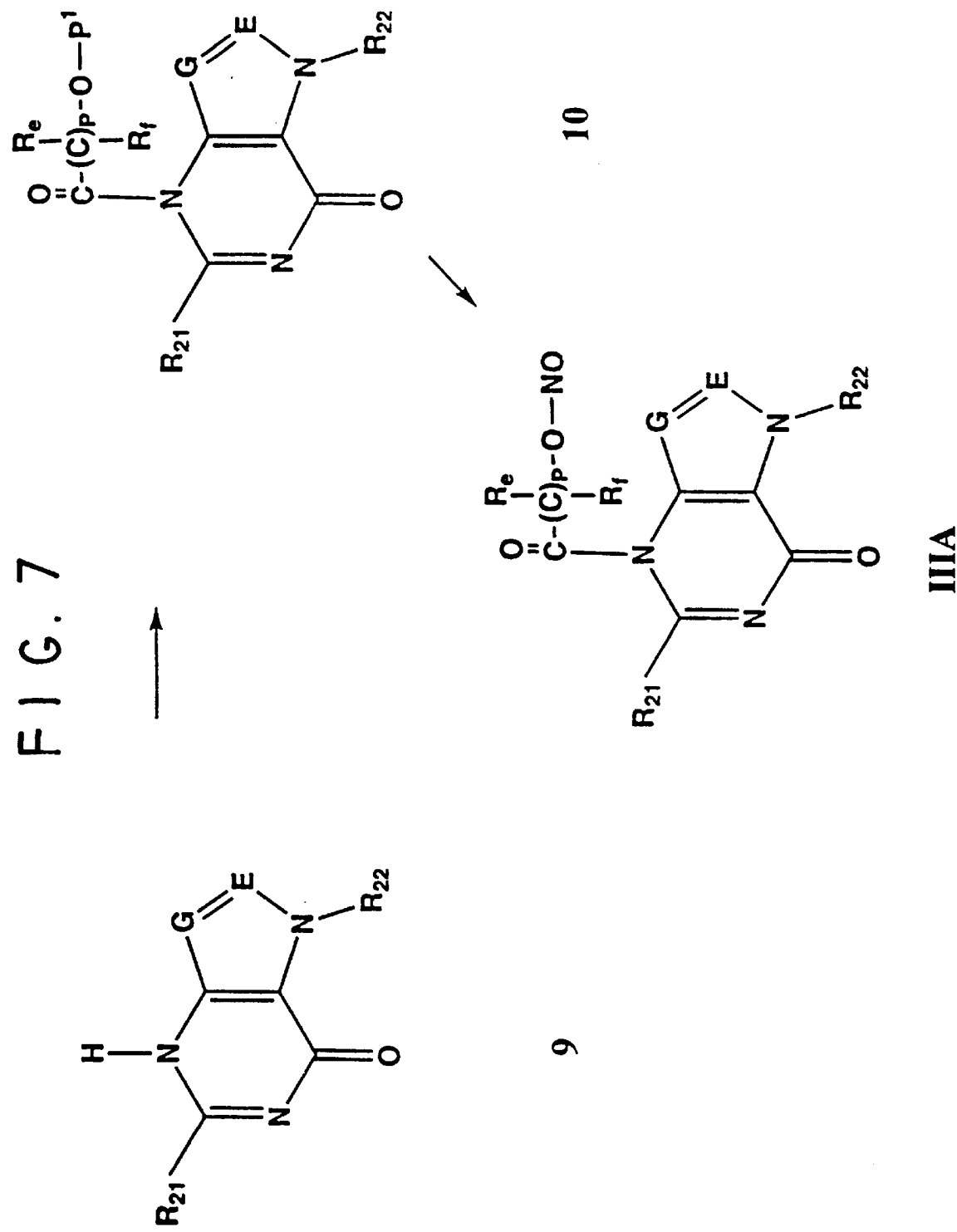
FIG. 7 Synthetic scheme for the preparation of nitrite containing purine-6-one derivatives.

Nitroso compounds of formula (III) wherein E, G, $R_{21}$, $R_{22}$, $R_e$, $R_f$, and p are defined as in this specification and a nitrite containing amide is representative of the $R_{11}$ group as defined in this specification may be prepared as outlined in FIG. 7. The purine-6-one group of formula 9 is converted to the acylated purine-6-one of formula 10 wherein p, $R_e$ and $R_f$ are defined as in this specification by reaction with an appropriate protected alcohol containing activated acylating agent wherein $P^1$ is as defined in this specification. Preferred methods for the formation of acylated purine-6-ones are reacting the purine-6-one with the preformed acid chloride or symmetrical anhydride of the protected alcohol containing acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DME, or acetonitrile with or without an amine base such as pyridine or triethylamine affords the compound of the formula IIIA.

Figure 8:
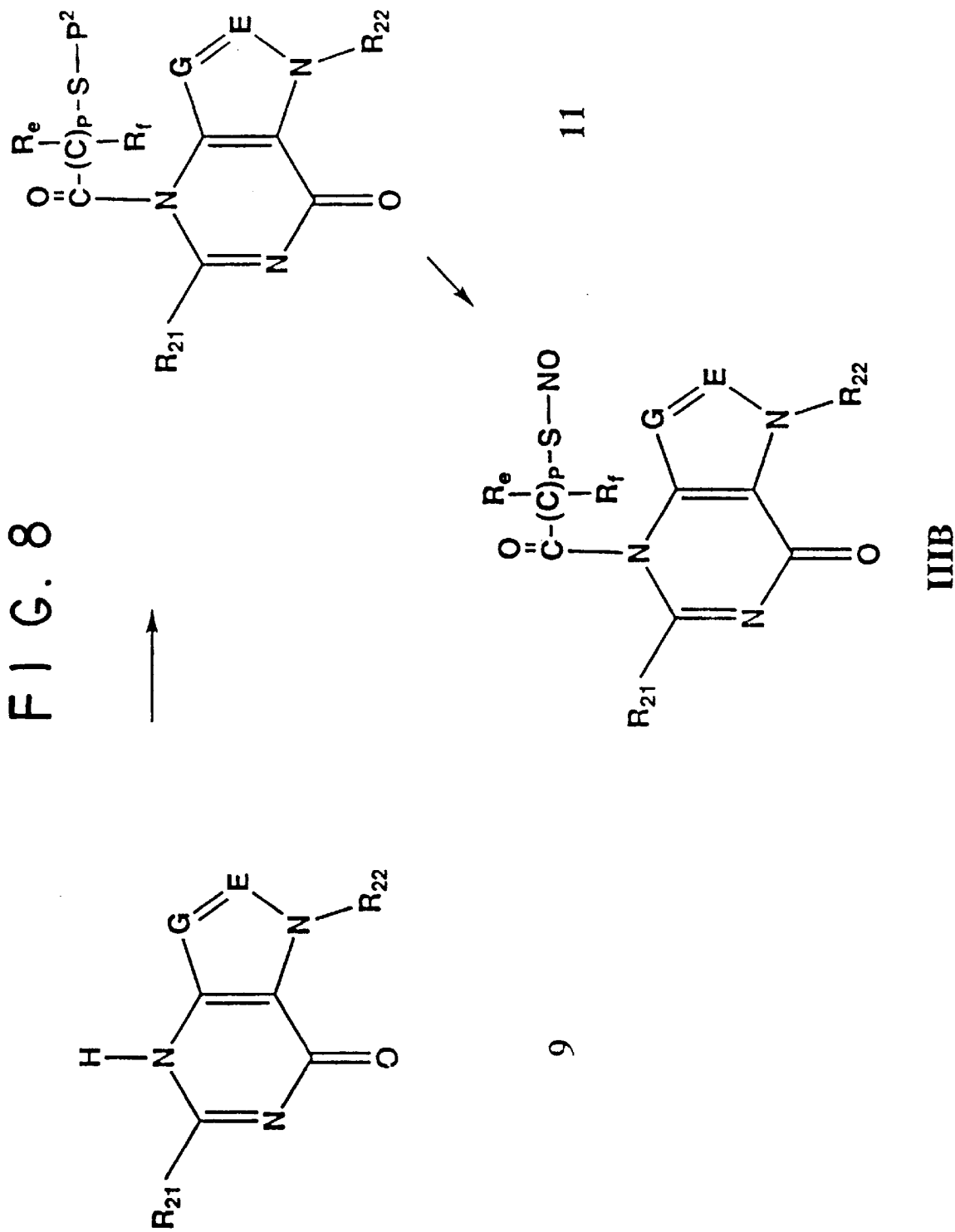
FIG. 8 Synthetic scheme for the preparation of nitrosothiol containing purine-6-one derivatives.

Nitroso compounds of formula (III) wherein E, G, $R_{21}$, $R_{22}$, $R_e$, $R_f$, and p are defined as in this specification and an nitrosothiol containing amide is representative of the $R_{11}$ group as defined in this specification may be prepared as outlined in FIG. 8. The purine-6-one group of formula 9 is converted to the acylated purine-6-one of formula 11 wherein p, $R_e$ and $R_f$ are defined as in this specification by reaction with an appropriate protected thiol containing activated acylating agent wherein $P^2$ is as defined in this specification. Preferred methods for the formation of acylated purine-6-ones are reacting the purine-6-one with the preformed acid chloride or symmetrical anhydride of the protected alcohol containing acid. Preferred protecting groups for the thiol moiety are as a thioester such as a thioacetate or thiobenzoate, as a disulfide, as a thiocarbamate such as N-methoxyrnethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IIIB. Alternatively, treatment of the deprotected thiol derived from compound 11 with a stoichiometric quantity of sodium nitrite in an acidic aqueous or alcoholic solution affords the compound of the formula IIIB.

Figure 9:
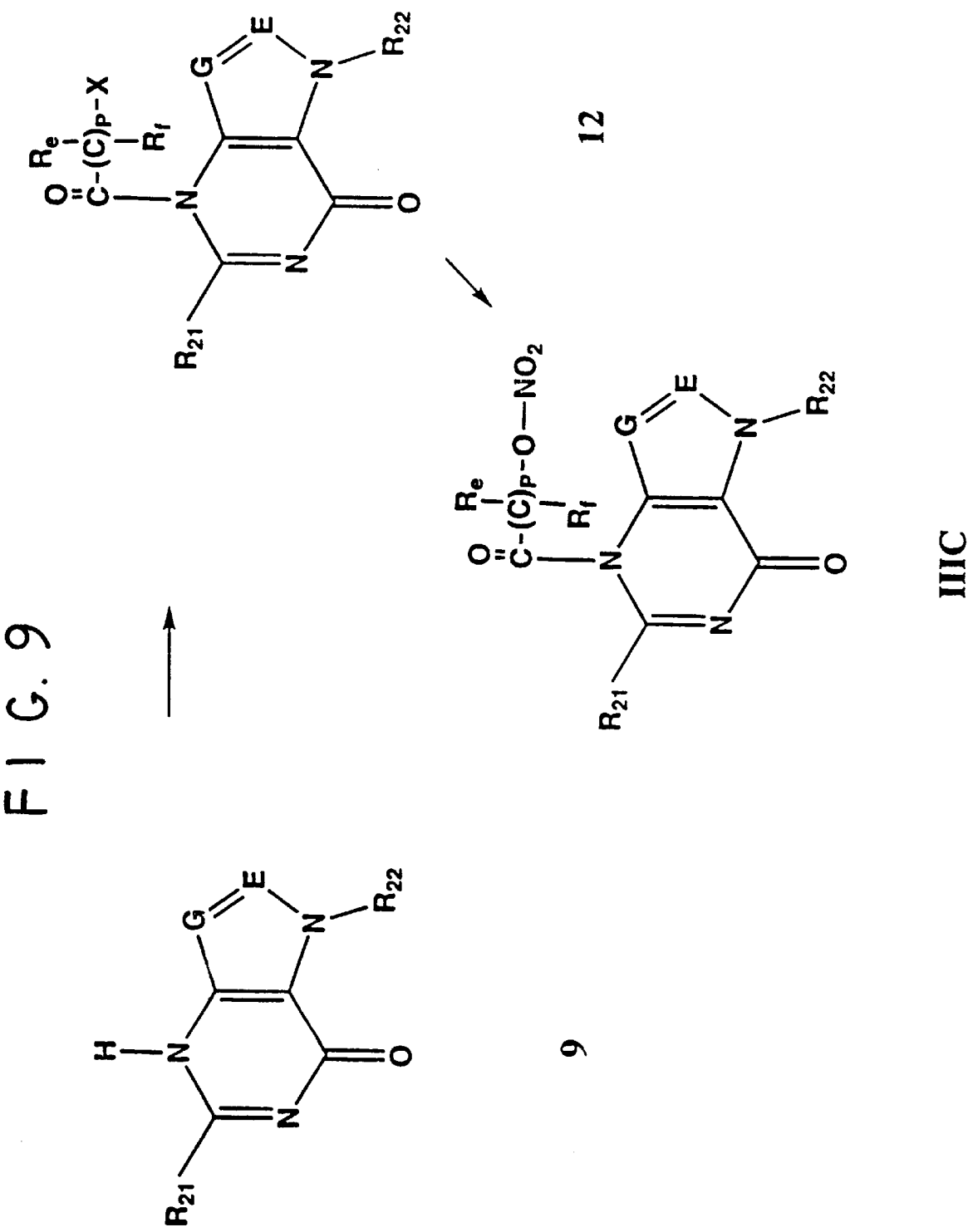
FIG. 9 Synthetic scheme for the preparation of nitrate containing purine-6-one derivatives.

Nitro compounds of formula (III) wherein E, G, $R_{21}$, $R_{22}$, $R_e$, $R_f$, and p are defined as in this specification and an nitrate containing amide is representative of the $R_{11}$ group as defined in this specification may be prepared as outlined in FIG. 9. The purine-6-one of formula 9 is converted to the acylated purine-6-one the of formula 12 wherein p, $R_e$ and $R_f$ are defined and X is halogen. Preferred methods for the formation of acylated purine-6-ones are reacting the purine-6-one with the preformed acid chloride or symmetrical anhydride of the halide containing acid. Preferred halides are bromide and iodide. Reaction of the of the acylated purine-6-one of the formula 12 with a suitable nitrating agent such as silver nitrate in an inert solvent such as acetonitrile affords the compound of the formula IIIC.

Another embodiment of this aspect provides processes for making compounds having structures IV and to the intermediates useful in such processes as follows.

Figure 10:
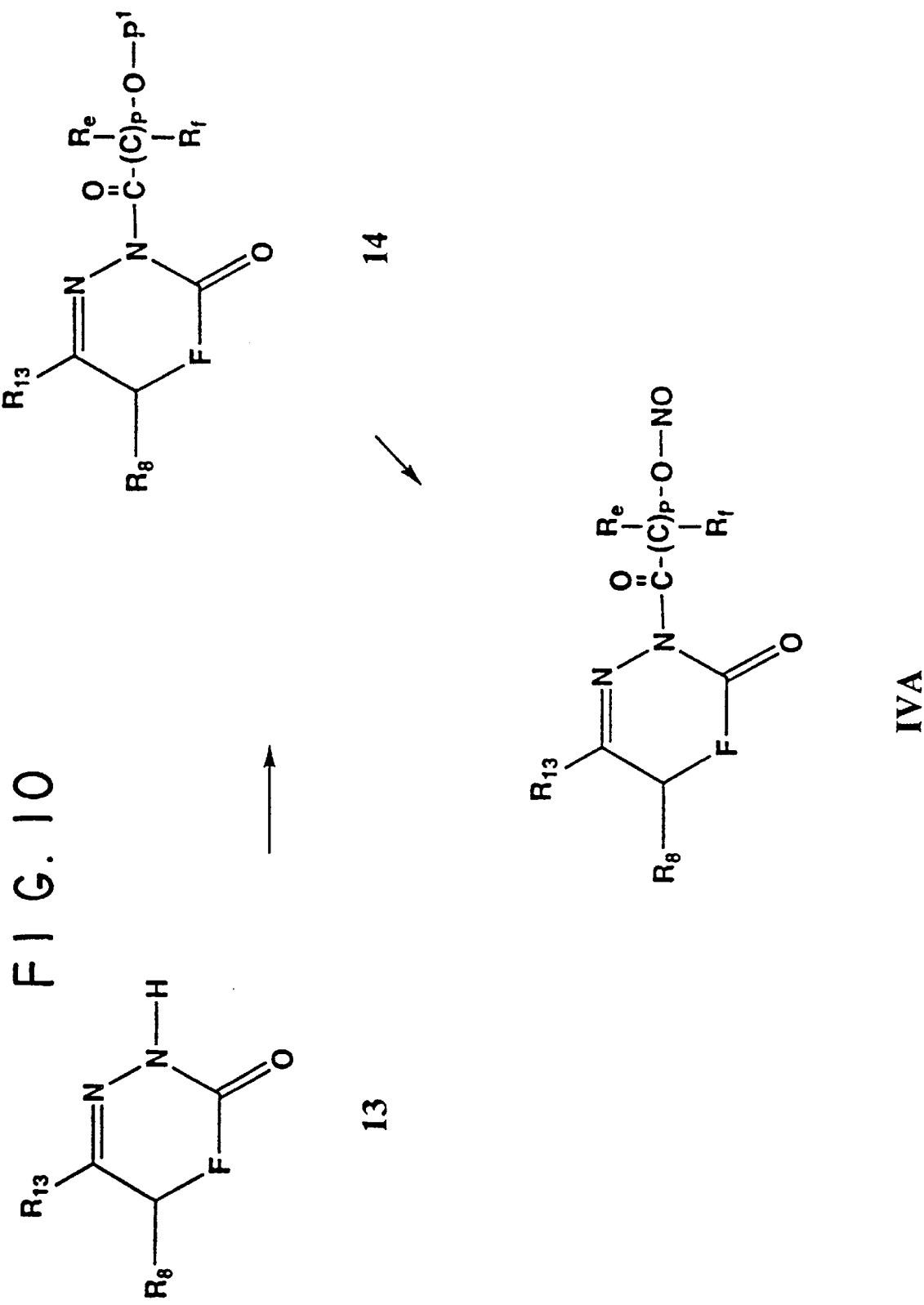
FIG. 10 Synthetic scheme for the preparation of nitrite containing pyrimidin-4-one derivatives.

Nitroso compounds of formula (IV) wherein F, $R_8$, $R_{13}$, $R_e$, $R_f$, and p are defined as in this specification and a nitrite containing acyl hydrazide is representative of the $R_4$ group as defined in this specification may be prepared as outlined in FIG. 10. The 3 (2-H)-pyridazinone or 2H-1, 2, 3, 4-thiadiazine of formula 13 is converted to the 3 (2-acyl)-pyridazinone or 2-acyl-1, 2, 3, 4-thiadiazine of formula 14 wherein p, $R_e$ and $R_f$ are defined as in this specification by reaction with an appropriate protected alcohol containing activated acylating agent wherein $P^1$ is as defined in this specification. Preferred methods for the formation of 3 (2-acyl)-pyridazinone or 2-acyl-1, 2, 3, 4-thiadiazine are reacting the 3 (2H-pyridazinone or 2H-1, 2, 3, 4-thiadiazine with the preformed acid chloride or symmetrical anhydride of the protected alcohol containing acid or condensing the 3 (2-H)-pyridazinone or 2H-1, 2, 3, 4-thiadiazine and protected alcohol containing acid in the presence of a dehydrating agent such as DCC or EDAC·HCl with a catalyst such as DMAP or HOBt. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IVA.

Nitroso compounds of formula (IV) wherein F, $R_8$, $R_{13}$, $R_e$, $R_f$, and p are defined as in this specification and a nitrosothiol containing acyl hydrazide is representative of the $R_4$ group as defined in this specification may be prepared as outlined in FIG. 11. The 3 2-H)-pyridazinone or 2H-1, 2, 3, 4-thiadiazine of formula 13 is converted to the 3 (2-acyl) -pyridazinone or 2-acyl-1, 2, 3, 4-thiadiazine of formula 15 wherein p, $R_e$ and $R_f$ are defined as in this specification by reaction with an appropriate protected thiol containing activated acylating agent wherein $P^2$ is as defined in this specification. Preferred methods for the formation of 3 (2-acyl)-pyridazinones or 2-acyl-1, 2, 3, 4-thiadiazines are reacting the 3 (2-H)-pyridazinone or 2H-1, 2, 3, 4-thiadiazine with the preformed acid chloride or symmetrical anhydride of the protected thiol containing acid or condensing the 3 (2-H)-pyridazinone or 2H-1, 2, 3, 4-thiadiazine and protected thiol containing acid in the presence of a dehydrating agent such as DCC or EDAC·HCl with a catalyst such as DMAP or HOBt. Preferred protecting groups for the thiol moiety are as a thioester such as a thioacetate or thiobenzoate, as a disulfide, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IVB. Alternatively, treatment of the deprotected thiol derived from compound 15 with a stoichiometric quantity of sodium nitrite in an acidic aqueous or alcoholic solution affords the compound of the formula IVB.

Figure 12:
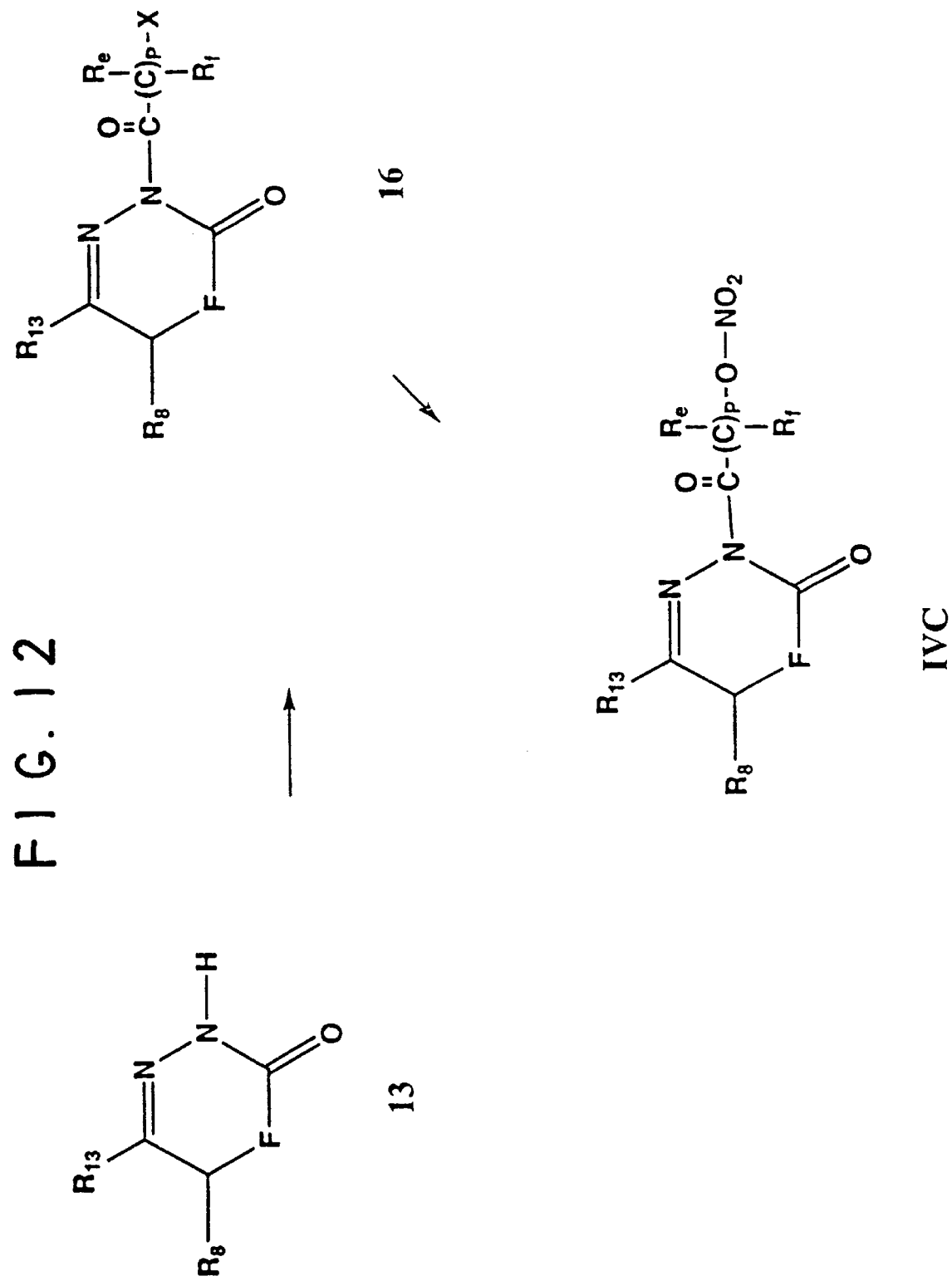
FIG. 12 Synthetic scheme for the preparation of nitrate containing pyrimidin-4-one derivatives.

Nitro compounds of formula (IV) wherein F, $R_8$, $R_{13}$, $R_e$, $R_f$, and p are defined as in this specification and an nitrate containing acyl hydrazide is representative of the $R_4$ group as defined in this specification may be prepared as outlined in FIG. 12. The 3 (2-H)-pyridazinone or 2H-1, 2, 3, 4-thiadiazine of formula 13 is converted to the 3 (2-acyl)-pyridazinone or 2-acyl-1, 2, 3, 4-thiadiazine of formula 16 wherein p, $R_e$ and $R_f$ are defined and X is halogen. Preferred methods for the formation of 3 (2-acyl)-pyridazinones or 2-acyl-1, 2, 3, 4-thiadiazines are reacting the 3 (2-H)-pyridazinone or 2H-1, 2, 3, 4-thiadiazine with the preformed acid chloride or symmetrical anhydride of the halide containing acid or condensing the 3 (2-H)-pyridazinone or 2H-1, 2, 3, 4-thiadiazine and halide containing acid in the presence of a dehydrating agent such as DCC or EDAC·HCl with a catalyst such as DMAP or HOBt. Preferred halides are bromide and iodide. Reaction of the 3 (2-acyl)-pyridazinone or 2-acyl-1, 2, 3, 4-thiadiazine of formula 16 with a suitable nitrating agent such as silver nitrate in an inert solvent such as acetonitrile affords the compound of the formula IVC.

Another embodiment of this aspect provides processes for making compounds having structures V and to the intermediates useful in such processes as follows.

Figure 13:
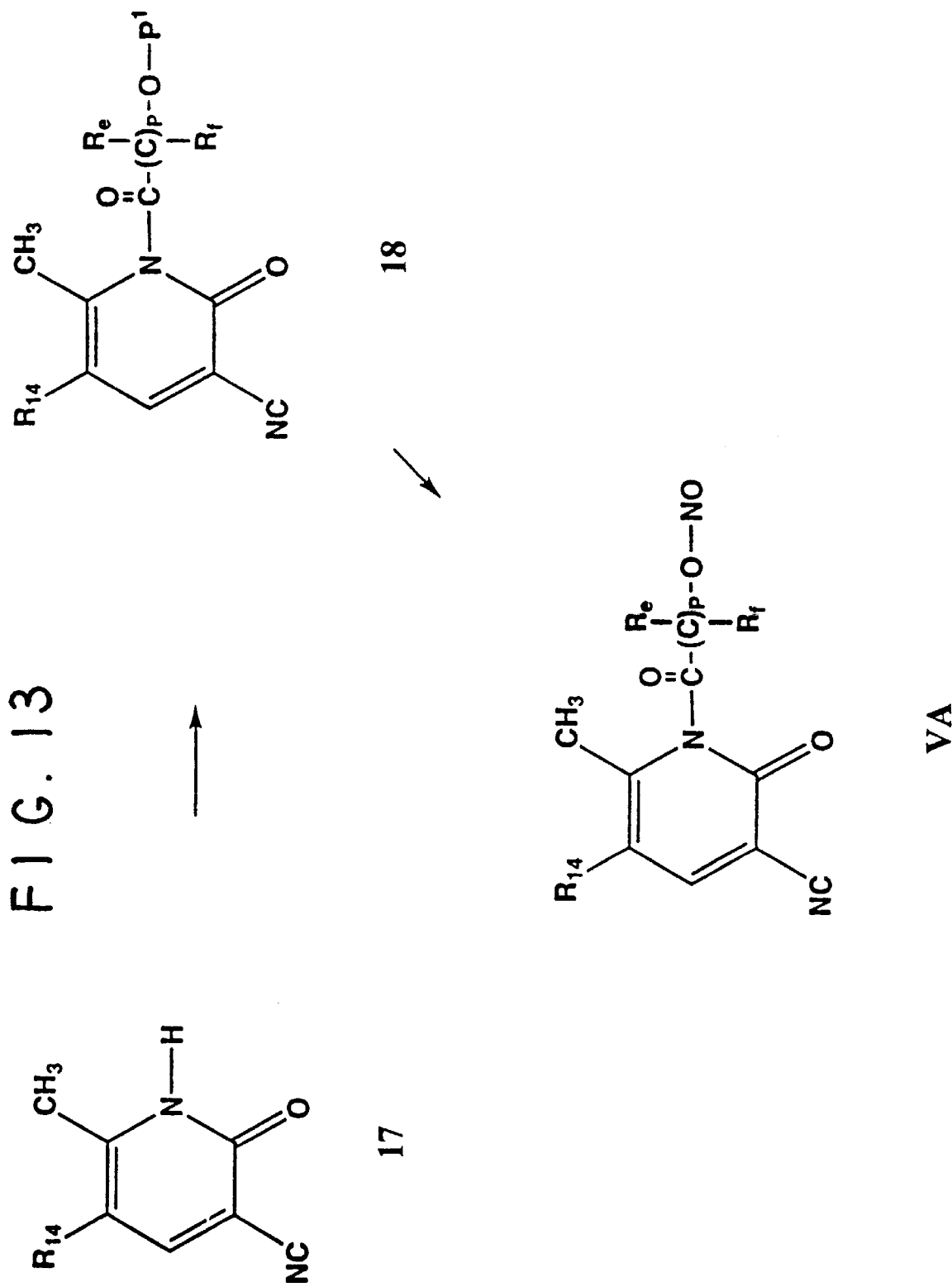
FIG. 13 Synthetic scheme for the preparation of nitrite containing 2-pyridone derivatives.

Nitroso compounds of formula (V) wherein $R_{14}$, $R_e$, $R_f$, and p are defined as in this specification and an nitrite containing imide is representative of the $R_4$ group as defined in this specification may be prepared as outlined in FIG. 13. The amide group of formula 17 is converted to the imide of formula 18 wherein p, $R_e$ and $R_f$ are defined as in this specification by reaction with an appropriate protected alcohol containing activated acylating agent wherein $P^1$ is as defined in this specification. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VA.

Figure 14:
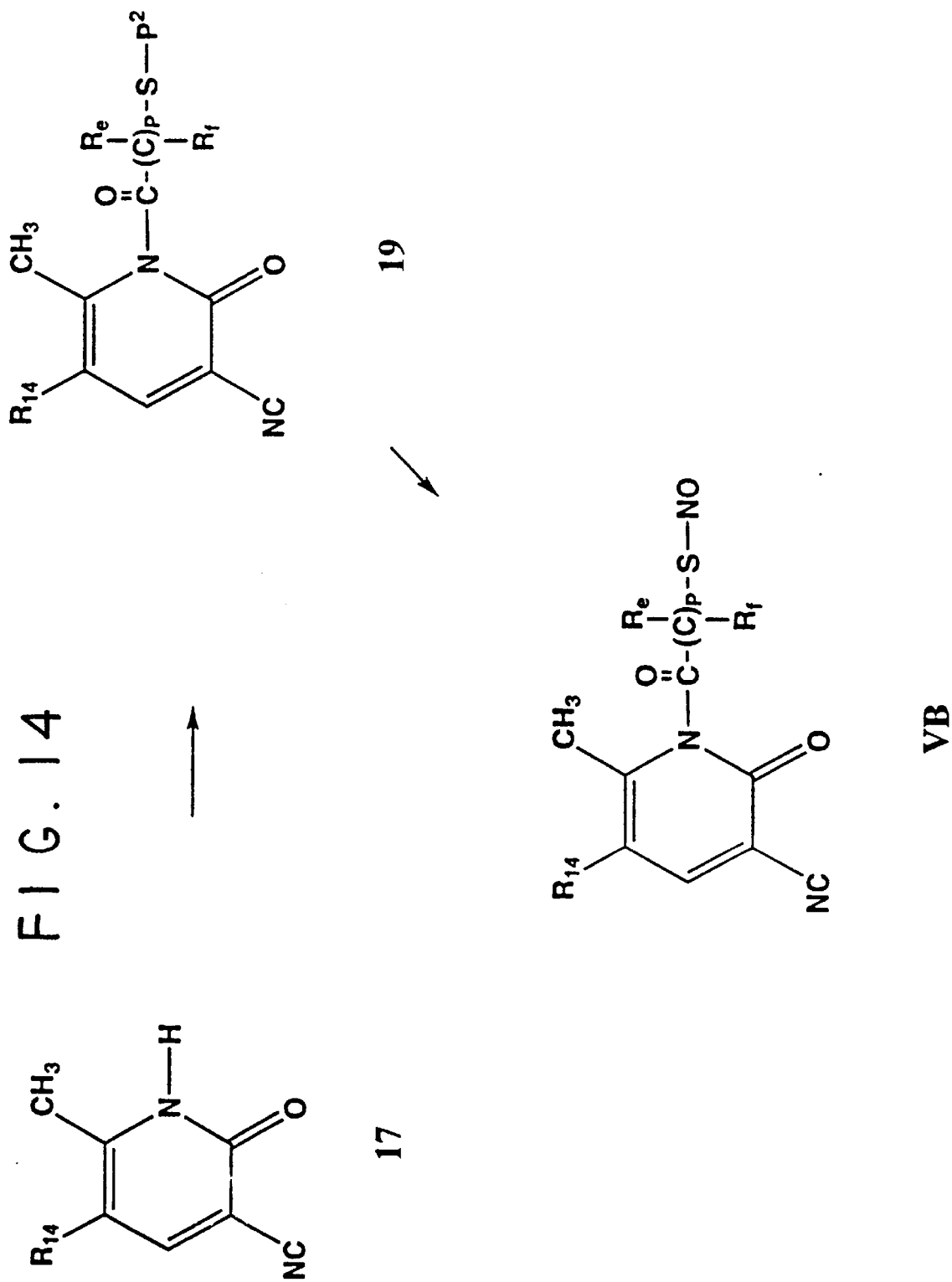
FIG. 14 Synthetic scheme for the preparation of nitrosothiol containing 2-pyridone derivatives.

Nitroso compounds of formula (V) wherein $R_{14}$, $R_e$, $R_f$, and p are defined as in this specification and a nitrosothiol containing imide is representative of the $R_4$ group as defined in this specification may be prepared as outlined in FIG. 14. The amide group of formula 17 is converted to the imide of formula 19 wherein p, $R_e$ and $R_f$ are defined as in this specification by reaction with an appropriate protected thiol containing activated acylating agent wherein $P^2$ is as defined in this specification. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VB. Alternatively, treatment of the deprotected thiol derived from compound 19 with a stoichiometric quantity of sodium nitrite in an acidic aqueous or alcoholic solution affords the compound of the formula VB.

Figure 15:
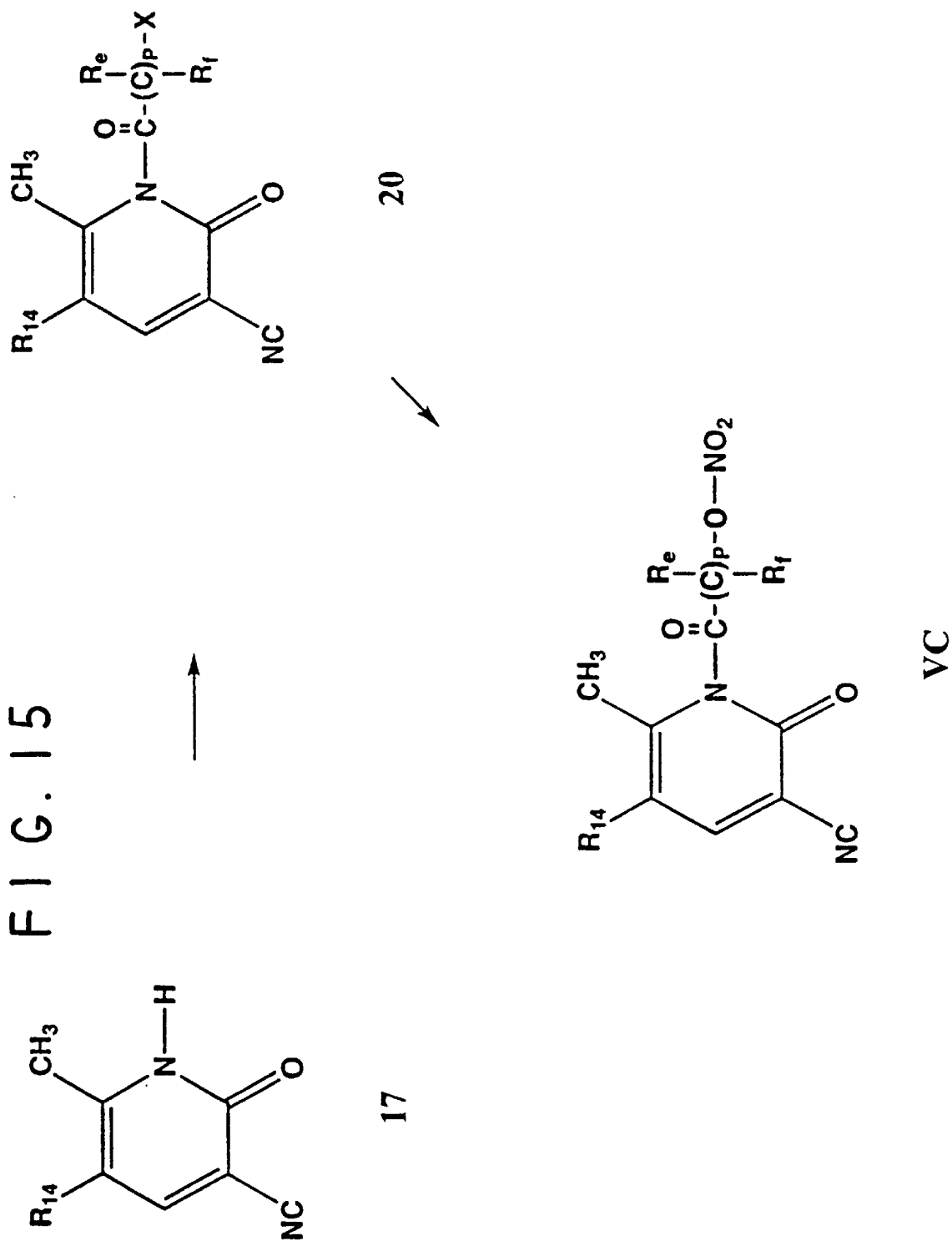
FIG. 15 Synthetic scheme for the preparation of nitrate containing 2-pyridone derivatives.

Nitro compounds of formula (V) wherein $R_{14}$, $R_e$, $R_f$, and p are defined as in this specification and a nitrate containing imide is representative of the $R_4$ group as defined in this specification may be prepared as outlined in FIG. 15. The amide group of the formula 17 is converted to the imide of the formula 20 wherein p, $R_e$ and $R_f$ are defined as in this specification and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 20 with a suitable nitrating agent such as silver nitrate in an inert solvent such as acetonitrile affords the compound of the formula VC.

Another embodiment of this aspect provides processes for making compounds having structures VI and to the intermediates useful in such processes as follows.

Figure 16:
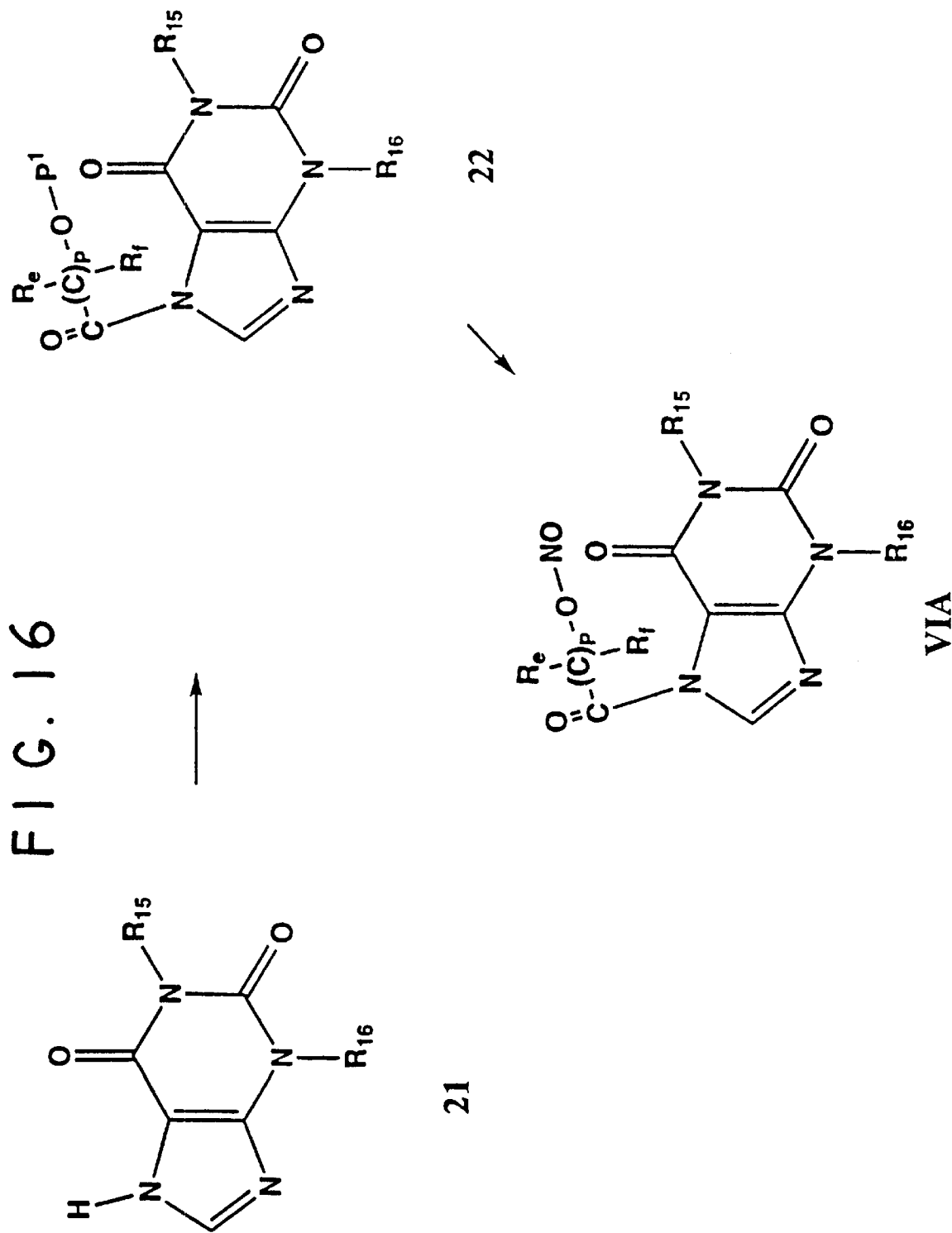
FIG. 16 Synthetic scheme for the preparation of nitrite containing purine-2,6-dione derivatives.

Nitroso compounds of formula (VI) wherein $R_{15}$, $R_{16}$, $R_e$, $R_f$, and p are defined as in this specification and a nitrite containing acyl imidazolide is representative of the $R_{17}$ group as defined in this specification may be prepared as outlined in FIG. 16. The 1H-purine-2, 6-dione of formula 21 is converted to the acylated derivative of the formula 22 wherein p, $R_e$ and $R_f$ are defined as in this specification by reaction with an appropriate protected alcohol containing activated acylating agent wherein $P^1$ is as defined in this specification. Preferred methods for the formation of acylated 1H-purine-2, 6-diones are reacting the 1H-purine-2, 6-dione with the preformed acid chloride or symmetrical anhydride of the protected alcohol containing acid or condensing the 1H-purine-2, 6-dione and protected alcohol containing acid in the presence of a dehydrating agent such as DCC or EDAC·HCl with a catalyst such as DMAP or HOBt. Preferred protecting groups for the alcohol moiety are silyl ethers such as a tert-butyldimethylsilyl ether or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIA.

Nitroso compounds of formula (VI) wherein $R_{15}$, $R_{16}$, $R_e$, $R_f$, and p are defined as in this specification and a nitrosothiol containing acyl imidazolide is representative of the $R_{17}$ group as defined in this specification may be prepared as outlined in FIG. 17. The 1H-purine-2, 6-dione of formula 21 is converted to the acylated derivative of the formula 23 wherein p, $R_e$ and $R_f$ are defined as in this specification by reaction with an appropriate protected thiol containing activated acylating agent wherein $P^2$ is as defined in this specification. Preferred methods for the formation of acylated 1H-purine-2, 6-diones are reacting the 1H-purine-2, 6-dione with the preformed acid chloride or symmetrical anhydride of the protected thiol containing acid or condensing the 1H-purine-2, 6-dione and protected thiol containing acid in the presence of a dehydrating agent such as DCC or EDAC·HCl with a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIB. Alternatively, treatment of the deprotected thiol derived from compound 23 with a stoichiometric quantity of sodium nitrite in an acidic aqueous or alcoholic solution affords the compound of the formula VIB.

Figure 18:
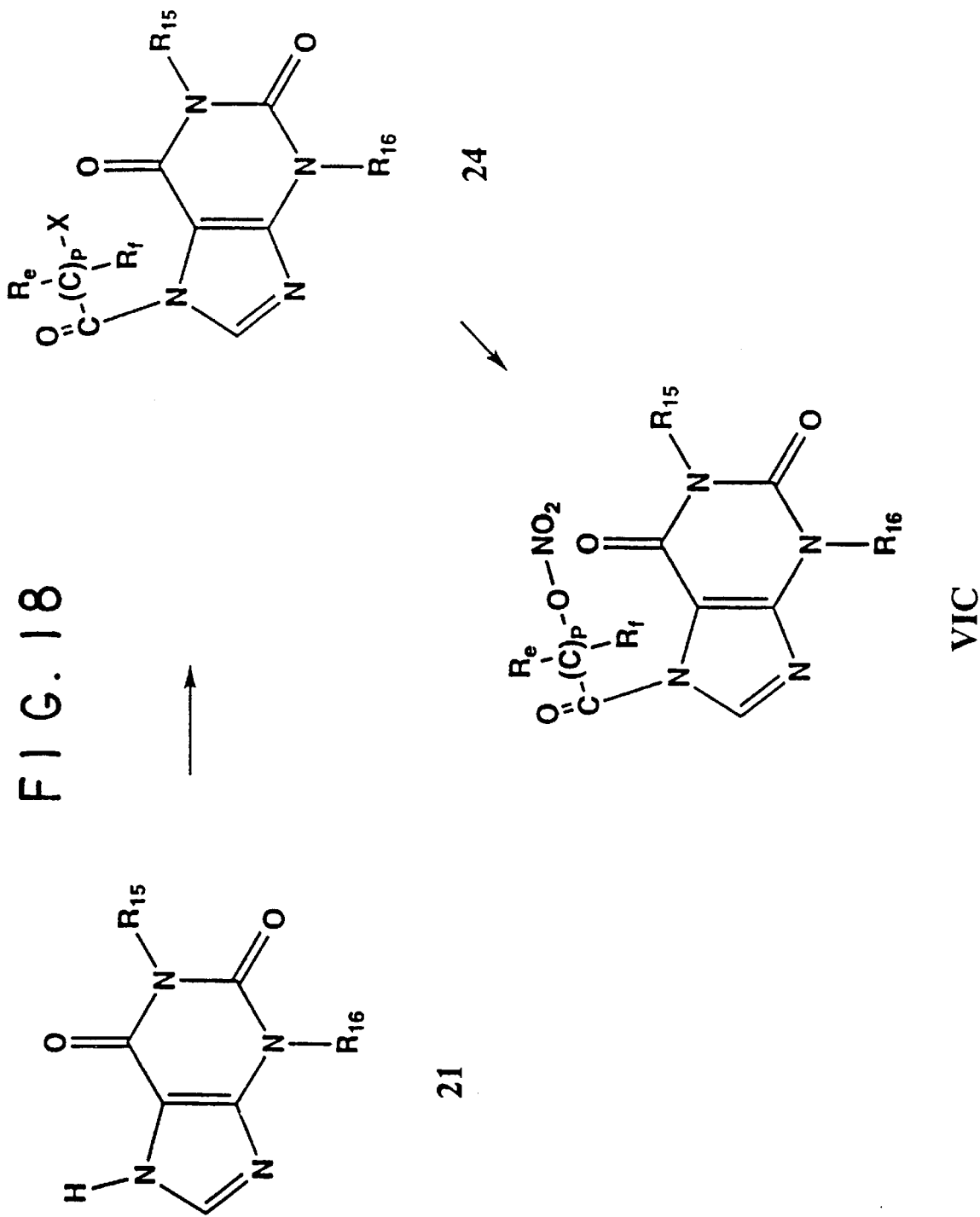
FIG. 18 Synthetic scheme for the preparation of nitrate containing purine-2,6-dione derivatives.

Nitro compounds of formula (VI) wherein $R_{15}$, $R_{16}$, $R_e$, $R_f$, and p are defined as in this specification and an O-nitrosated acylated 1H-purine-2, 6-dione is representative of the $R_{17}$ group as defined in this specification may be prepared as outlined in FIG. 18. The 1H-purine-2, 6-dione of the formula 21 is converted to the acylated derivative of the formula 24 wherein p, $R_e$ and $R_f$ are defined as in this specification and X is a halogen by reaction with an appropriate halide containing activated acylating agent. Preferred methods for the formation of acylated 1H-purine-2, 6-diones are reacting the 1H-purine-2, 6-dione with the preformed acid chloride or symmetrical anhydride of the halide containing acid or condensing the 1H-purine-2, 6-dione and halide containing acid in the presence of a dehydrating agent such as DCC or EDAC·HCl with a catalyst such as DMAP or HOBt. Preferred halides are bromide and iodide. Reaction of the acylated 1H-purine-2, 6-dione of the formula 24 with a suitable nitrating agent such as silver nitrate in an inert solvent such as acetonitrile affords the compound of the formula VIC.

Another embodiment of this aspect provides processes for making compounds having structures VII and to the intermediates useful in such processes as follows.

Figure 19:
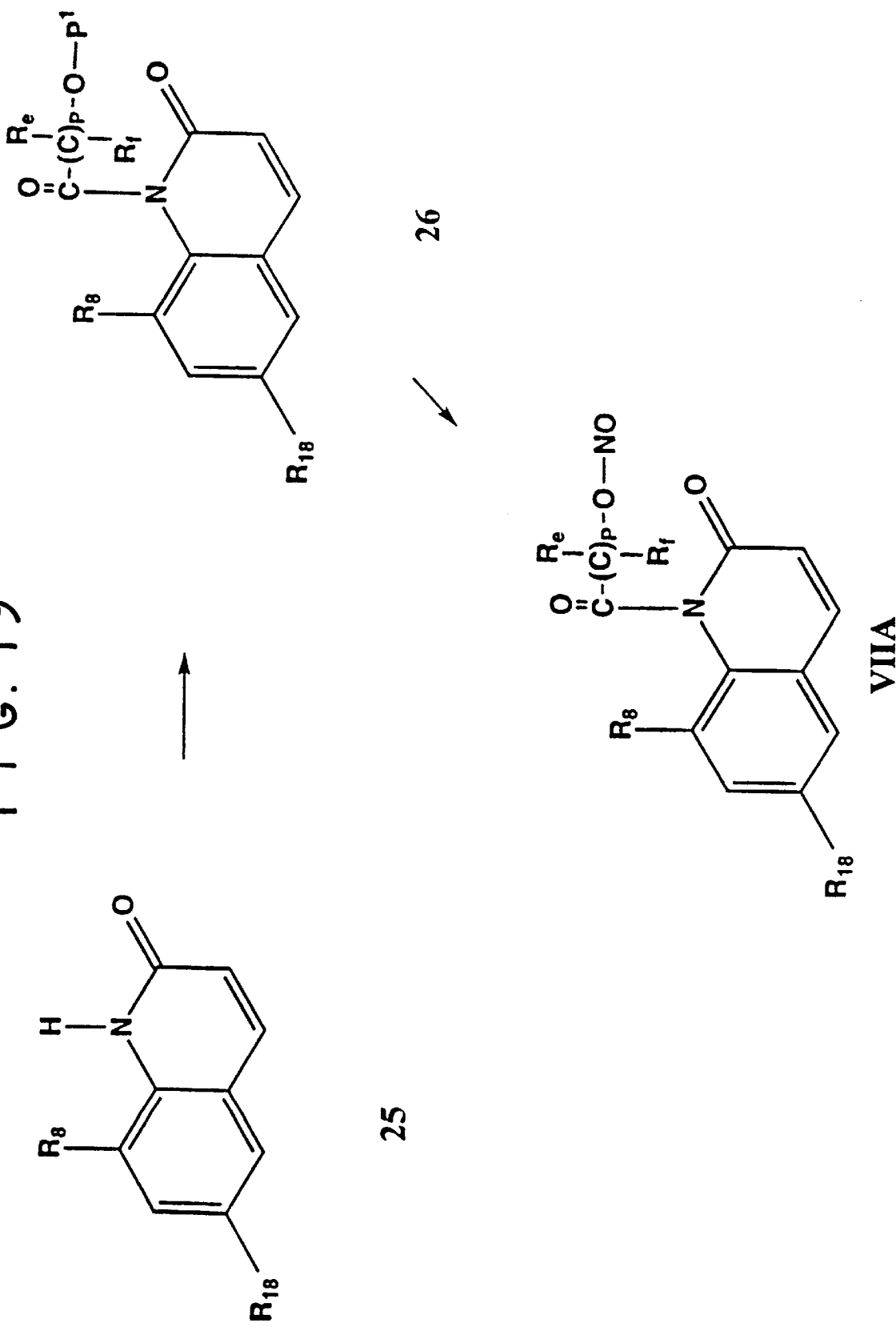
FIG. 19 Synthetic scheme for the preparation of nitrite containing quinoline derivatives.

Nitroso compounds of formula (VII) wherein $R_8$, $R_{18}$, $R_e$, $R_f$, and p are defined as in this specification and a nitrite containing imide is representative of the $R_4$ group as defined in this specification may be prepared as outlined in FIG. 19. The amide nitrogen of formula 25 is converted to the imide of formula 26 wherein p, $R_e$ and $R_f$ are defined as in this specification by reaction with an appropriate protected alcohol containing activated acylating agent wherein $P^1$ is as defined in this specification. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIIA.

Nitroso compounds of formula (VII) wherein $R_8$, $R_{18}$, $R_e$, $R_f$, and p are defined as in this specification and a nitrosothiol containing imide is representative of the $R_4$ group as defined in this specification may be prepared as outlined in FIG. 20. The amide nitrogen of formula 25 is converted to the imide of formula 27 wherein p, $R_e$ and $R_f$ are defined as in this specification by reaction with an appropriate protected thiol containing activated acylating agent wherein $P^2$ is as defined in this specification. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIIB. Alternatively, treatment of the deprotected thiol derived from compound 27 with a stoichiometric quantity of sodium nitrite in an acidic aqueous or alcoholic solution affords the compound of the formula VIIB.

Nitro compounds of formula (VII) wherein $R_8$, $R_{18}$, $R_e$, $R_f$, and p are defined as in this specification and a nitrate containing imide is representative of the $R_4$ group as defined in this specification may be prepared as outlined in FIG. 21.

The amide group of the formula 25 is converted to the imide of the formula 28 wherein p, $R_e$ and $R_f$ are defined as in this specification and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 28 with a suitable nitrating agent such as silver nitrate in an inert solvent such as acetonitrile affords the compound of the formula VIIC.

Another embodiment of this aspect provides processes for making compounds having structures VIII and to the intermediates useful in such processes as follows.

Figure 22:
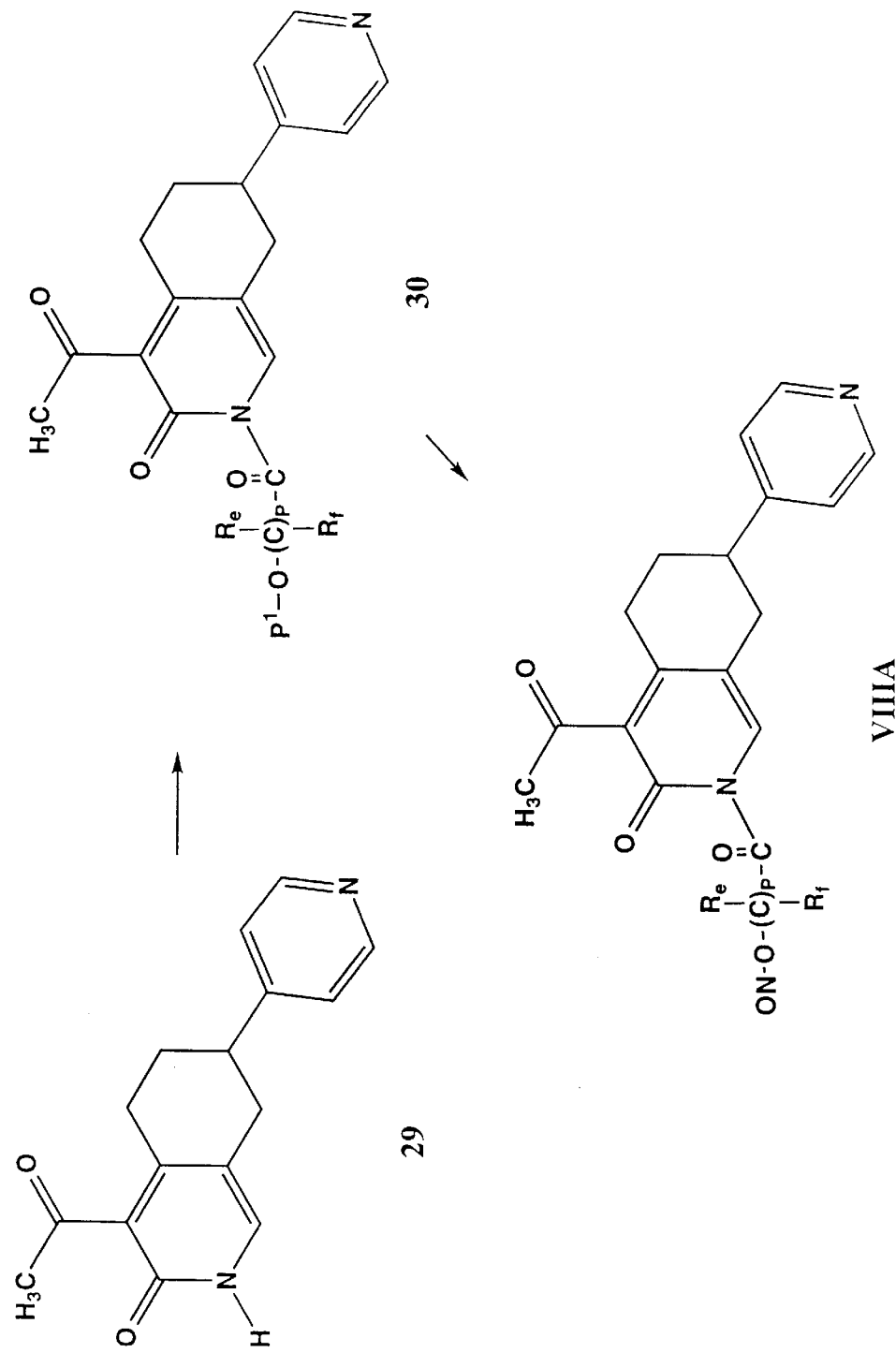
FIG. 22 Synthetic scheme for the preparation of nitrite containing substituted pyridine derivatives.

Nitroso compounds of formula (VIII) wherein $R_e$, $R_f$, and p are defined as in this specification and a nitrite containing imide is representative of the $R_{19}$ group as defined in this specification may be prepared as outlined in FIG. 22. The amide nitrogen of formula 29 is converted to the imide of formula 30 wherein p, $R_e$ and $R_f$ are defined as in this specification by reaction with an appropriate protected alcohol containing activated acylating agent wherein $P^1$ is as defined in this specification. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIIA.

Figure 23:
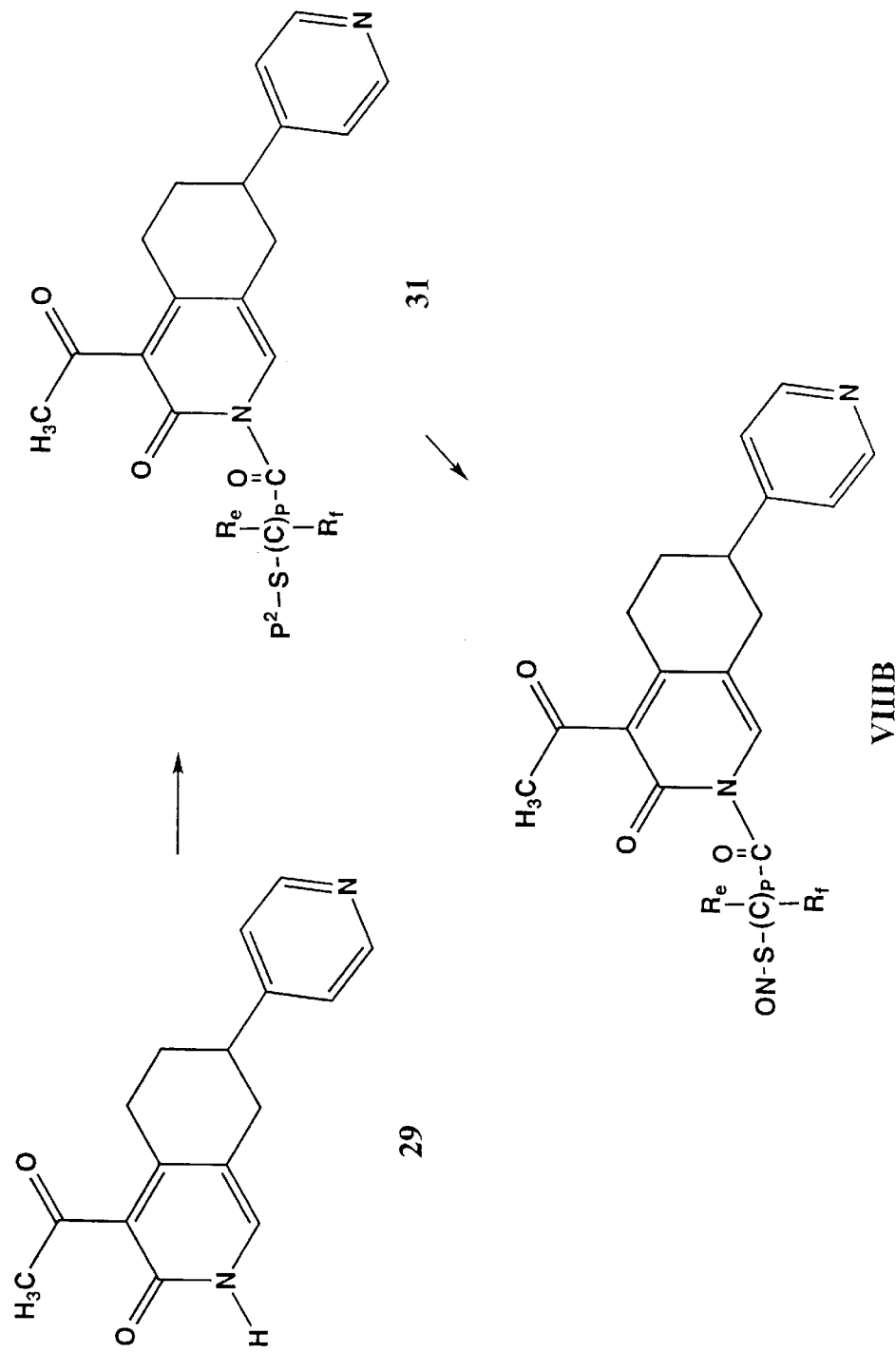
FIG. 23 Synthetic scheme for the preparation of nitrosothiol containing substituted pyridine derivatives.

Nitroso compounds of formula (VIII) wherein $R_e$, $R_f$, and p are defined as in this specification and a nitrosothiol containing imide is representative of the $R_{19}$ group as defined in this specification may be prepared as outlined in FIG. 23. The amide nitrogen of formula 29 is converted to the imide of formula 31 wherein p, $R_e$ and $R_f$ are defined as in this specification by reaction with an appropriate protected thiol containing activated acylating agent wherein $P^2$ is as defined in this specification. Preferred methods for the formation of imides are reacting the amide with the preformed acid chloride of the protected thiol containing acid in the presence of pyridine at low temperature or condensing the amide and protected alcohol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIIB. Alternatively, treatment of the deprotected thiol derived from compound 31 with a stoichiometric quantity of sodium nitrite in an acidic aqueous or alcoholic solution affords the compound of the formula VIIIB.

Figure 24:
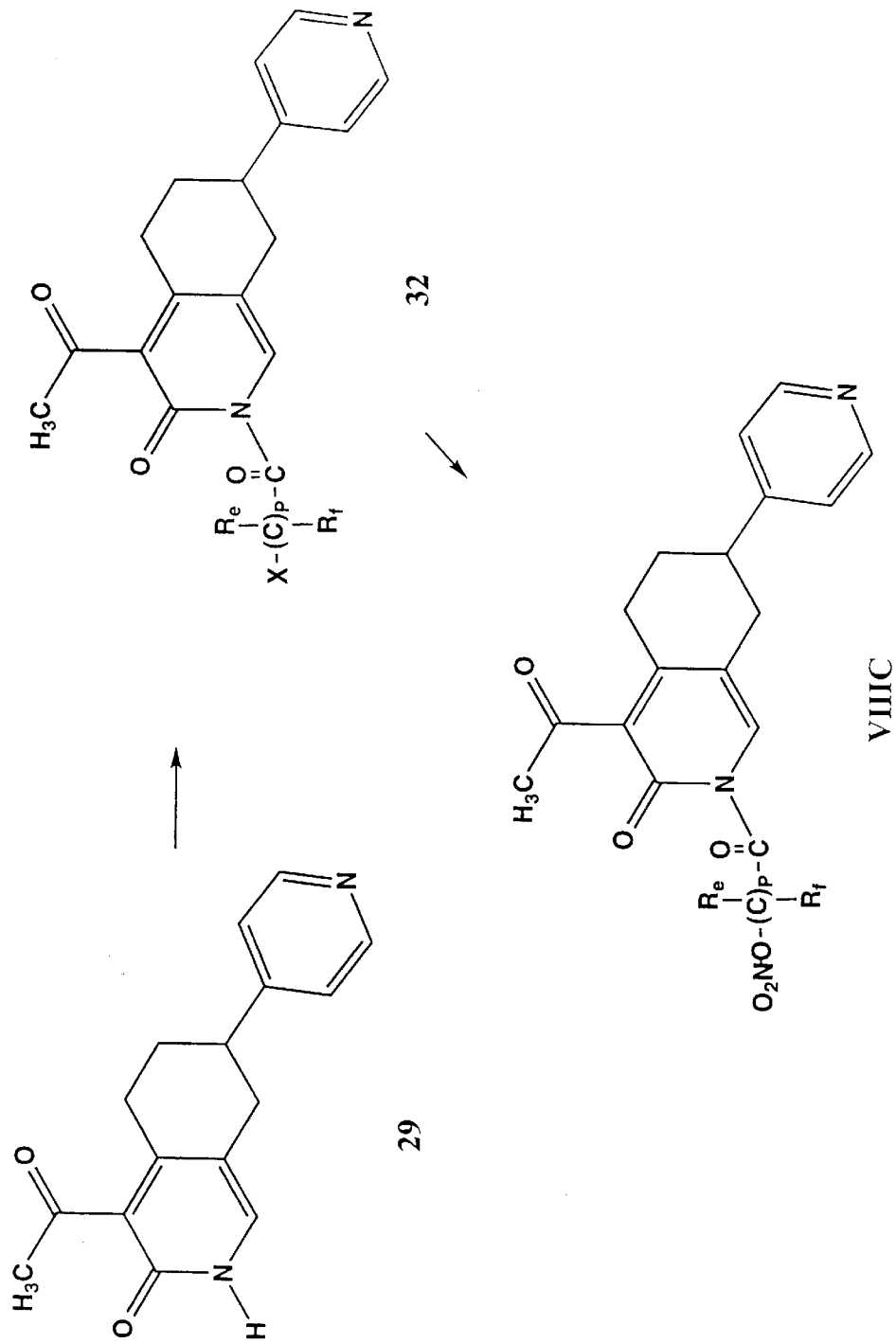
FIG. 24 Synthetic scheme for the preparation of nitrate containing substituted pyridine derivatives.

Nitro compounds of formula (VIII) wherein $R_e$, $R_f$, and p are defined as in this specification and a nitrate containing imide is representative of the $R_{19}$ group as defined in this specification may be prepared as outlined in FIG. 24. The amide group of the formula 29 is converted to the imide of the formula 32 wherein p, $R_e$ and $R_f$ are defined as in this specification and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 32 with a suitable nitrating agent such as silver nitrate in an inert solvent such as acetonitrile affords the compound of the formula VIIIC.

Another embodiment of this aspect provides processes for making compounds having structures IX and to the intermediates useful in such processes as follows.

Figure 25:
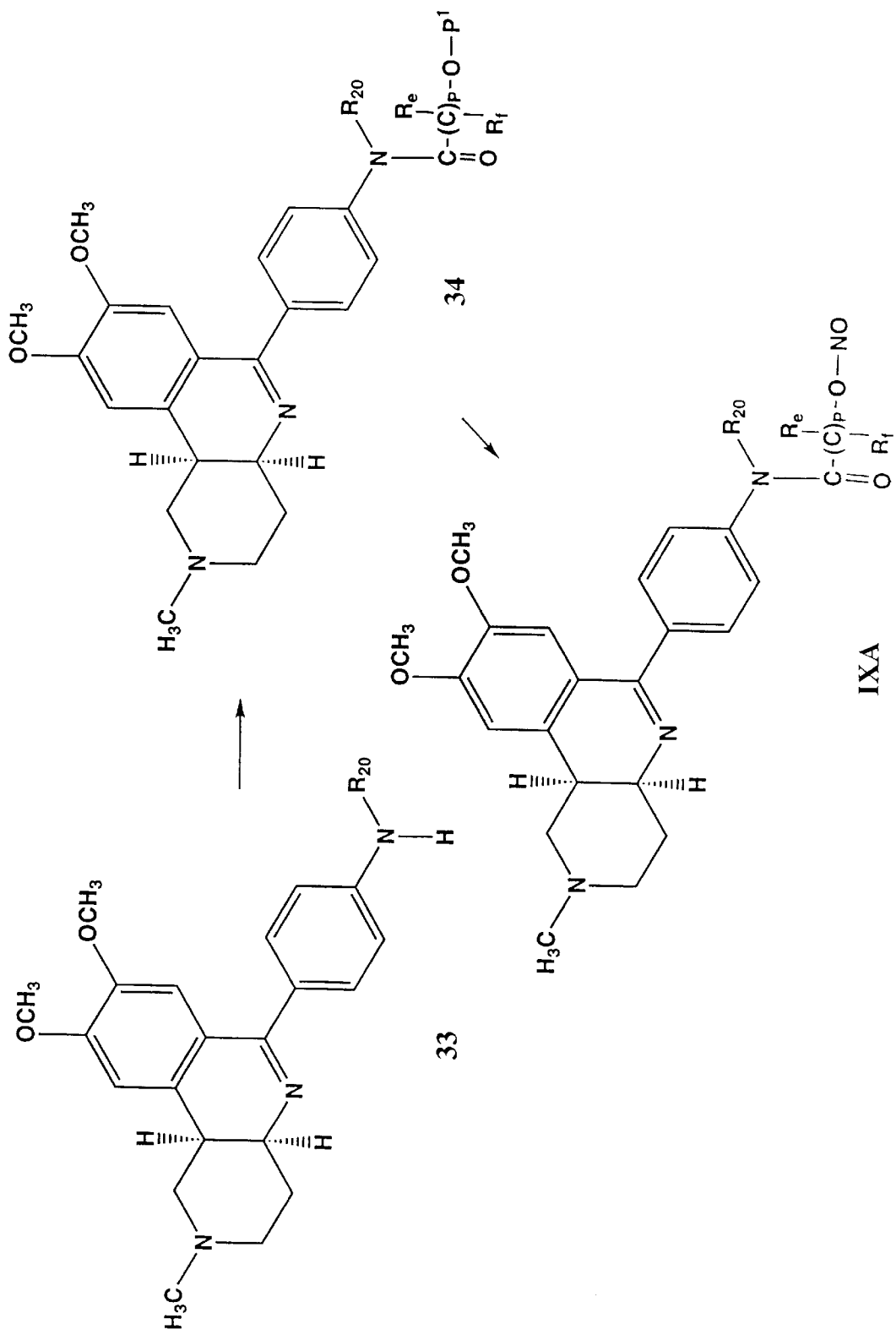
FIG. 25 Synthetic scheme for the preparation of nitrite containing benzo[c] [1,6]naphthyridine derivatives.

Nitroso compounds of formula (IX) wherein $R_{20}$, $R_e$, $R_f$, and p are defined as in this specification and an nitrate containing imide or sulfonimide is representative of the $R_4$ group as defined in this specification may be prepared as outlined in FIG. 25. The amide or sulfonamide nitrogen of formula 33 is converted to the imide or sulfonimide of formula 34 wherein p, $R_e$ and $R_f$ are defined as in this specification by reaction with an appropriate protected alcohol containing activated acylating agent wherein $P^1$ is as defined in this specification. Preferred methods for the formation of imides or sulfonimides are reacting the amide or sulfonimide with the preformed acid chloride of the protected alcohol containing acid in the presence of pyridine at low temperature or condensing the amide or sulfonimide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IXA.

Figure 26:
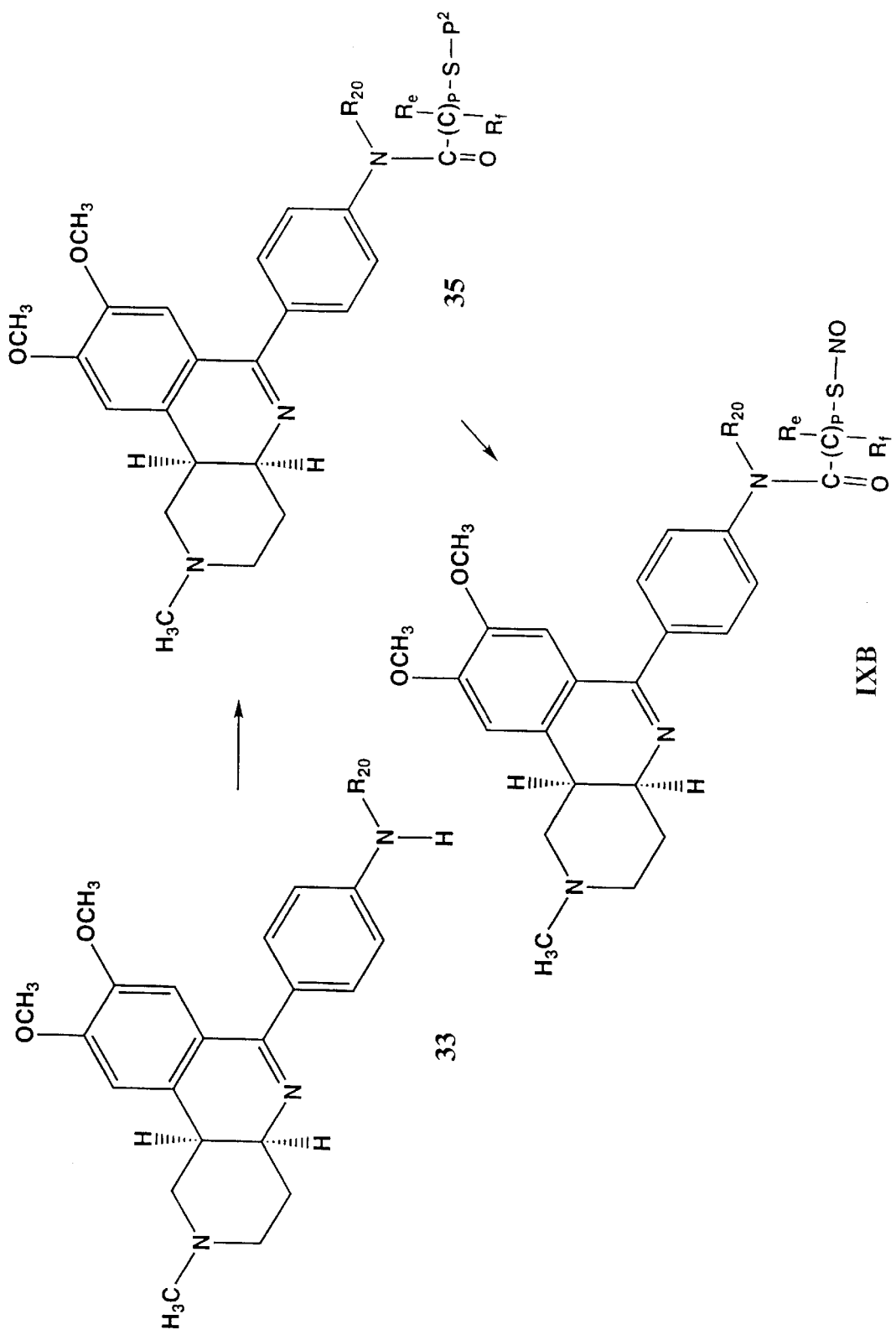
FIG. 26 Synthetic scheme for the preparation of nitrosothiol containing benzo[c] [1,6]naphthyridine derivatives.

Nitroso compounds of formula (IX) wherein $R_{20}$, $R_e$, $R_f$, and p are defined as in this specification and an nitrosothiol containing imide or sulfonimide is representative of the $R_4$ group as defined in this specification may be prepared as outlined in FIG. 26. The amide or sulfonamide nitrogen of formula 33 is converted to the imide or sulfonimide of formula 35 wherein p, $R_e$ and $R_f$ are defined as in this specification by reaction with an appropriate protected thiol containing activated acylating agent wherein $P^2$ is as defined in this specification. Preferred methods for the formation of imides or sulfonimides are reacting the amide or sulfonimide with the preformed acid chloride of the protected thiol containing acid in the presence of pyridine at low temperature or condensing the amide or sulfonimide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IXB. Alternatively, treatment of the deprotected thiol derived from compound 35 with a stoichiometric quantity of sodium nitrite in an acidic aqueous or alcoholic solution affords the compound of the formula IXB.

Figure 27:
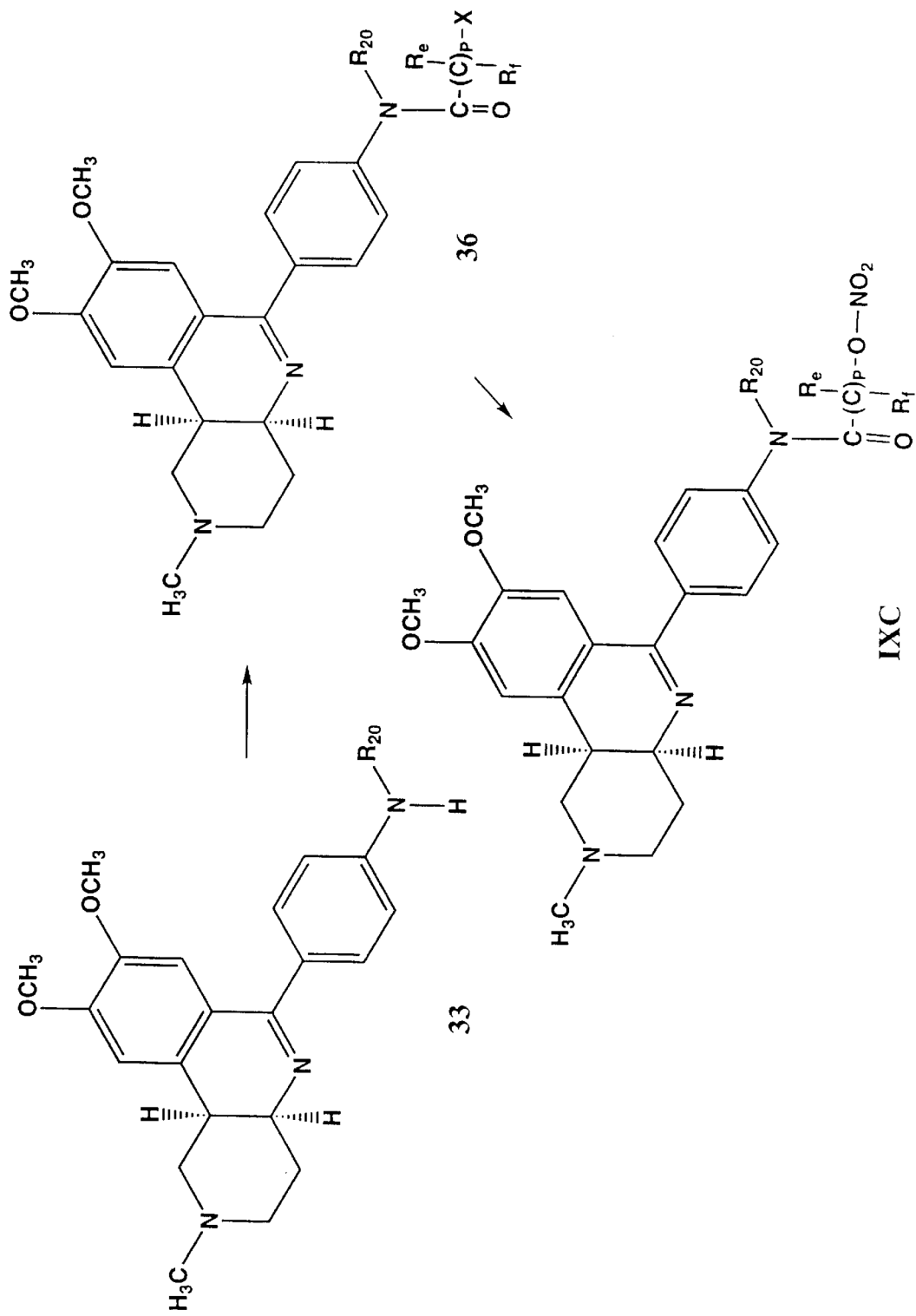
FIG. 27 Synthetic scheme for the preparation of nitrate containing benzo[c] [1,6]naphthyridine derivatives.
Figure 28:
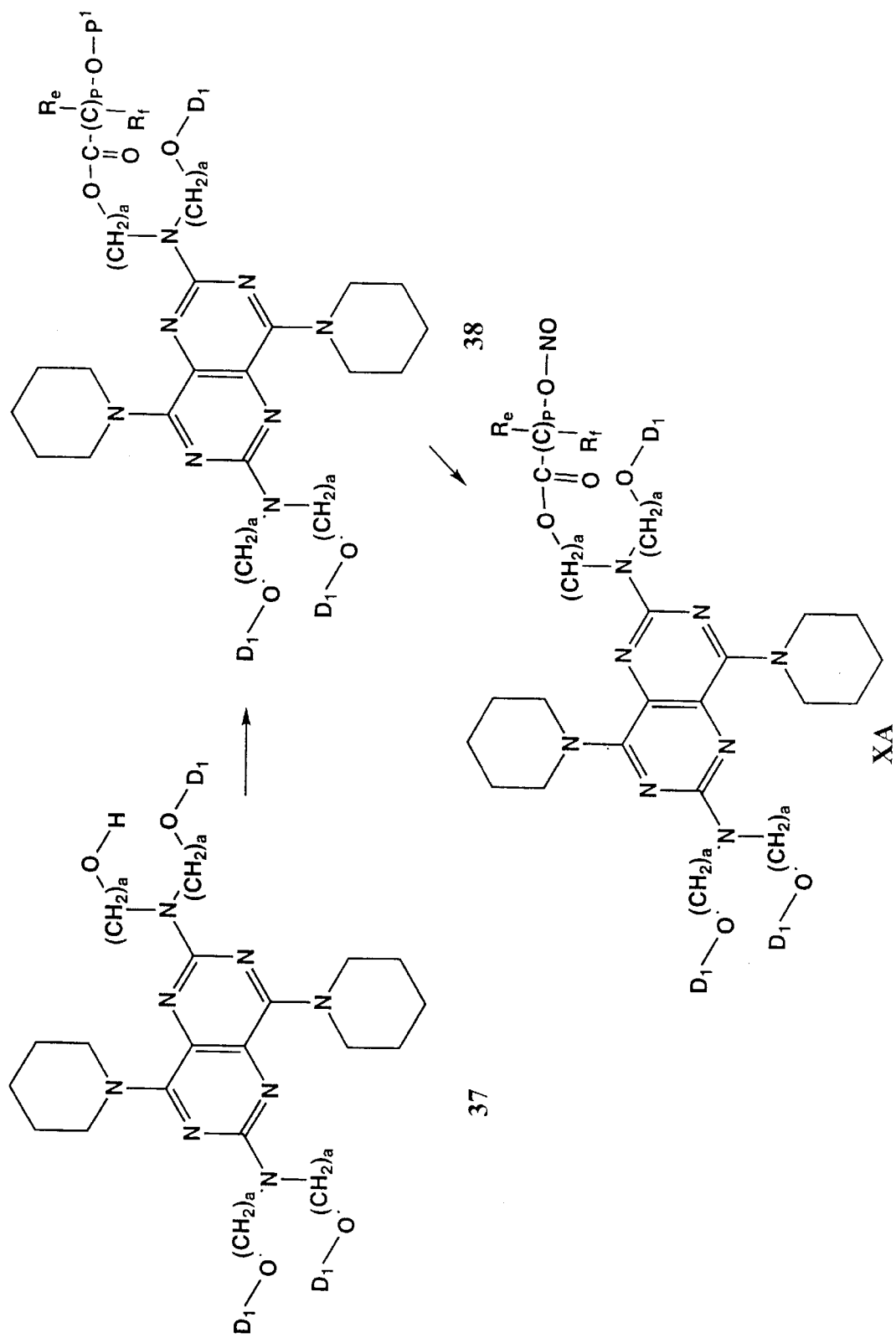
FIG. 28 Synthetic scheme for the preparation of nitrite containing 2,6-dihydroxyalkylamino-4,8-dipiperidino pyrimido [5,4-d]pyrimidine derivatives.
Figure 29:
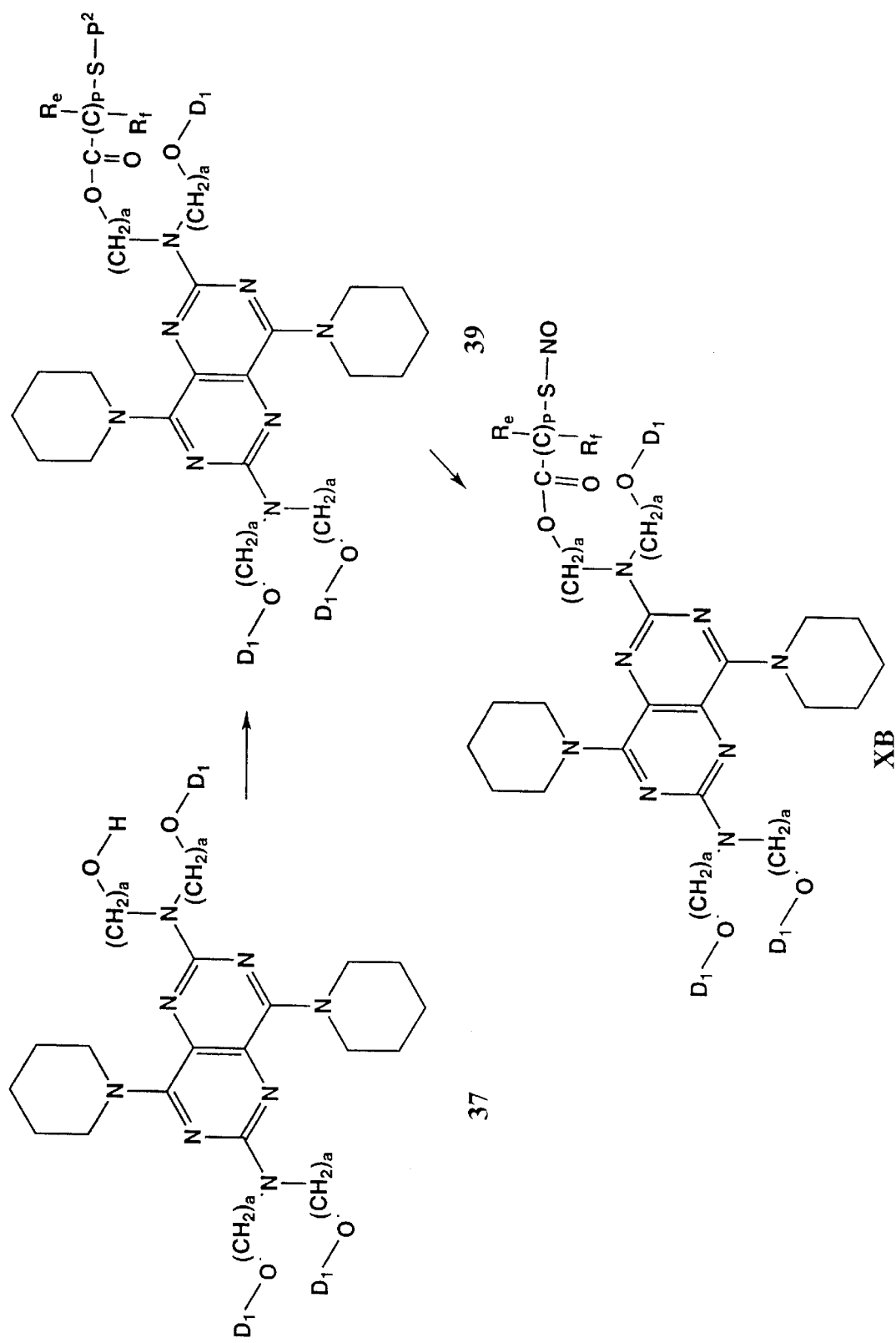
FIG. 29 Synthetic scheme for the preparation of nitrosothiol containing 2,6-dihydroxyalkylamino-4,8-dipiperidino pyrimido [5,4-d]pyrimidine derivatives.
Figure 30:
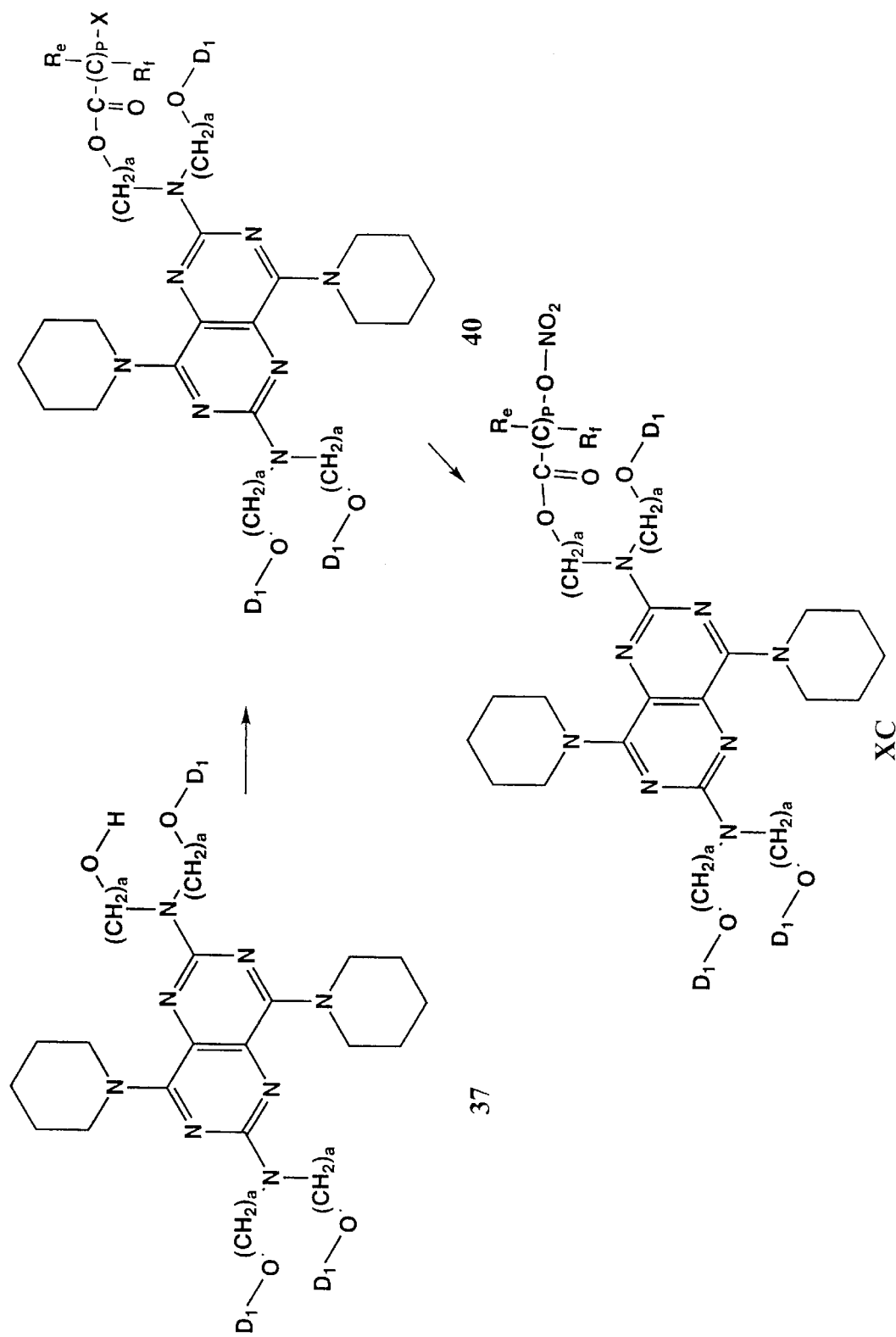
FIG. 30 Synthetic scheme for the preparation of nitrate containing 2,6-dihydroxyalkylamino-4,8-dipiperidino pyrimido [5,4-d]pyrimidine derivatives.

Nitro compounds of formula (IX) wherein $R_{20}$, $R_e$, $R_f$, and p are defined as in this specification and a nitrate containing imide or sulfonimide is representative of the $R_4$ group as defined in this specification may be prepared as outlined in FIG. 27. The amide or sulfonamide group of the formula 33 is converted to the imide or sulfonimide of the formula 36 wherein p, $R_e$ and $R_f$ are defined as in this specification and X is a halogen by reaction with an appropriate halide containing activated acylating agent. Preferred methods for the formation of imides or sulfonimides are reacting the amide or sulfonamide with the preformed acid chloride of the halide containing acid in the presence of pyridine at low temperature or condensing the amide or sulfonamide and halide containing symmetrical anhydride in the presence of a catalyst such as sulfuric acid. Preferred halides are bromide and iodide. Reaction of the imide or sulfonimide of the formula 36 with a suitable nitrating agent such as silver nitrate in an inert solvent such as acetonitrile affords the compound of the formula IXC.

Another embodiment of this aspect provides processes for making compounds having structures X and to the intermediates useful in such processes as follows.

Nitroso compounds of formula (X) wherein $D_1$, $R_e$, $R_f$, and p are defined as in this specification and a nitrite containing ester is representative of the D group as defined in this specification may be prepared according to Scheme 28. The alcohol group of formula 37 is converted to the ester of formula 38 wherein p, $R_e$ and $R_f$ are defined as in this specification by reaction with an appropriate protected alcohol containing activated acylating agent wherein $P^1$ is as defined in this specification. Preferred methods for the formation of esters are reacting the alcohol with the preformed acid chloride or symmetrical anhydride of the protected alcohol containing acid or condensing the alcohol and protected alcohol containing acid with a dehydrating agent such as DCC or EDAC·HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula XA.

Nitroso compounds of formula (X) wherein $D_1$, $R_e$, $R_f$, and p are defined as in this specification and a nitrosothiol containing ester is representative of the D group as defined in this specification may be prepared according to Scheme 29. The alcohol group of the formula 37 is converted to the ester of the formula 39 wherein p, $R_e$ and $R_f$ are defined as in this specification by reaction with an appropriate protected thiol containing activated acylating agent wherein $P^2$ is as defined in this specification. Preferred methods for the formation of esters are reacting the alcohol with the preformed acid chloride or symmetrical anhydride of the protected thiol containing acid or condensing the alcohol and protected thiol containing acid with a dehydrating agent such as DCC or EDAC·HCl in the presence of a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine affords the compound of the formula XB. Alternatively, treatment of the deprotected thiol derived from compound 39 with a stoichiometric quantity of sodium nitrite in aqueous or alcoholic acid affords the compound of the formula XB.

Nitro compounds of formula (X) wherein $D_1$, $R_e$, $R_f$, and p are defined as in this specification and a nitrate containing ester is representative of the D group as defined in this specification may be prepared according to Scheme 30. The alcohol group of the formula 37 is converted to the ester of the formula 40 wherein p, $R_e$ and $R_f$ are defined as in this specification and X is a halogen by reaction with an appropriate halide containing activated acylating agent. Preferred methods for the formation of esters are reacting the alcohol with the preformed acid chloride or symmetrical anhydride of the halide containing acid or condensing the alcohol and halide containing acid with a dehydrating agent such as DCC or EDAC·HCl in the presence of a catalyst such as DMAP or HOBt. Preferred halides are bromide and iodide. Reaction of the ester of the formula 40 with a suitable nitrating agent such as silver nitrate in an inert solvent such as acetonitrile affords the compound of the formula XC.

As noted above, another aspect the invention provides a composition comprising (i) a therapeutically effective amount of a PDE inhibitor, which optionally can be substituted with at least one NO or $NO_2$ group or a group that stimulates endogenous production of NO or EDRF in vivo, and (ii) a compound that donates, transfers or releases nitrogen monoxide as a charged species, i.e., nitrosonium ($NO^+$) or nitroxyl ($NO^-$), or as the neutral species, nitric oxide (NO•) and/or a compound that stimulates endogenous production of NO or EDRF in vivo.

The compounds that donate, transfer or release nitric oxide can be any of those known to the art, including those mentioned and/or exemplified below.

Nitrogen monoxide can exist in three forms: $NO^-$ (nitroxyl), NO• (nitric oxide) and $NO^+$ (nitrosonium). NO• is a highly reactive short-lived species that is potentially toxic to cells. This is critical, because the pharmacological efficacy of NO depends upon the form in which it is delivered. In contrast to NO•, nitrosonium and nitroxyl do not react with $O_2$ or $O_2^-$ species. Consequently, administration of NO equivalents does not result in the generation of toxic by-products or the elimination of the active NO moiety.

Compounds contemplated for use in the invention are nitric oxide and compounds that release nitric oxide or otherwise directly or indirectly deliver or transfer nitric oxide to a site of its activity, such as on a cell membrane, in vivo. As used here, the term "nitric oxide" encompasses uncharged nitric oxide (NO•) and charged nitric oxide species, particularly including nitrosonium ion ($NO^+$) and nitroxyl ion ($NO^-$). The reactive form of nitric oxide can be provided by gaseous nitric oxide. The nitric oxide releasing, delivering or transferring compounds, having the structure F—NO wherein F is a nitric oxide releasing, delivering or transferring moiety, include any and all such compounds which provide nitric oxide to its intended site of action in a form active for their intended purpose. As used here, the term "NO adducts" encompasses any of such nitric oxide releasing, delivering or transferring compounds, including, for example, S-nitrosothiols, S-nitrothiols, O-nitrosoalcohols, O-nitroalcohols, sydnonimines, 2-hydroxy-2-nitrosohydrazines (NONOates), (E)-alkyl-2-[(E)-hydroxyimino]-5-nitro-3-hexene amines or amides, nitrosoamines, as well a subtstates for the endogenous enzymes which synthesize nitric oxide. It is contemplated that any or all of these "NO adducts" can be mono- or poly-nitrosylated or nitrosated at a variety of naturally susceptible or artificially provided binding sites for nitric oxide or derivatives which donate or release NO.

One group of such NO adducts is the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars, S-nitrosylated-modified and unmodified oligonucleotides (preferably of at least 5, and more particularly 5–200, nucleotides); and an S-nitrosylated hydrocarbons where the hydrocarbon can be a branched or unbranched, and saturated or unsaturated aliphatic hydrocarbon, or an aromatic hydrocarbon; S-nitrosylated hydrocarbons having one or more substituent groups in addition to the S-nitroso group; and heterocyclic compounds. S-nitrosothiols and the methods for preparing them are described in U.S. Pat. No. 5,380,758; Oae et al., *Org. Prep. Proc. Int*, 15(3): 165–198 (1983); Loscalzo et al., *J Pharmacol. Exp. Ther.*, 249(3):726729 (1989) and Kowaluk et al., *J Pharmacol. Exp. Ther.*, 256:1256–1264 (1990), all of which are incorporated in their entirety by reference.

One particularly preferred embodiment of this aspect relates to S-nitroso amino acids where the nitroso group is linked to a sulfur group of a sulfur-containing amino acid or derivative thereof. For example, such compounds include the following: S-nitroso-N-acetylcysteine, S-nitroso-captopril, S-nitroso-homocysteine, S-nitroso-cysteine and S-nitroso-glutathione.

Suitable S-nitrosylated proteins include thiol-containing proteins (where the NO group is attached to one or more sulfur group on an amino acid or amino acid derivative thereof from various functional classes including enzymes, such as tissue-type plasminogen activator (TPA) and cathepsin B; transport proteins, such as lipoproteins, heme proteins such as hemoglobin and serum albumin; and biologically protective proteins, such as the immunoglobulins and the cytokines. Such nitrosylated proteins are described in PCT Publ. Applic. No. WO 93/09806, published May 27, 1993. Examples include polynitrosylated albumin where multiple thiol or other nucleophilic centers in the protein are modified.

Further examples of suitable S-nitrosothiols include those having the structures:

(i) $CH_3[C(R_e)(R_f)]_xSNO$ wherein x equals 2 to 20 and $R_e$ and $R_f$ are as defined in this specification;

(ii) $HS[C((R_e)(R_f)]_xSNO$ wherein x equals 2 to 20; and $R_e$ and $R_f$ are as defined in this specification;

(iii) $ONS[C(R_e)(R_f)]_xB$; and (iv) $H_2N$—$(CO_2H)$—$(CH_2)_x$—$C(O)NH$—$C(CH_2SNO)$—$C(O)NH$—$CH_2$—$CO_2H$ wherein x equals 2 to 20; $R_e$ and $R_f$ are as defined in this specification; and B is selected from the group consisting of fluoro, $C_1$–$C_6$ alkoxy, cyano, carboxamido, cycloalkyl, arylalkoxy, alkylsulfinyl, arylthio, alkylamino, dialkylamino, hydroxy, carbamoyl, N-alkylcarbamoyl, N,N-dialkylcarbamoyl, amino, hydroxyl, carboxyl, hydrogen, nitro and aryl.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) to yield the S-nitroso derivative. Acids which may be used for this purpose include aqueous sulfuric, acetic and hydrochloric acids. Alternatively, the precursor thiol may be nitrosylated by treatment with an alkyl nitrite such as tert-butyl nitrite.

Another group of such NO adducts are those wherein the compounds donate, transfer or release nitric oxide and are selected from the group consisting of compounds that include at least one ON—N— or ON—C— group. The compound that includes at least one ON—N— or ON—C— group is preferably selected from the group consisting of ON—N— or ON—C-polypeptides (the term "polypeptide" includes proteins and also polyamino acids that do not possess an ascertained biological function, and derivatives thereof); ON—N— or ON—C-amino acids(including natural and synthetic amino acids and their stereoisomers and racemic mixtures); ON—N— or ON—C-sugars; ON—N— or ON—C-modified and unmodified oligonucleotides (preferably of at least 5, and more particularly 5–200, nucleotides), ON—O—, ON—N— or ON—C-hydrocarbons which can be branched or unbranched, saturated or unsaturated aliphatic hydrocarbons or aromatic hydrocarbons; ON—N— or ON—C— hydrocarbons having one or more substituent groups in addition to the ON—N— or ON—C— group; and ON—N— or ON—C-heterocyclic compounds.

Another group of such NO adducts is the nitrites which have an —O—NO group wherein the organic template to which the nitrite group is appended is a protein, polypeptide, amino acid, carbohydrate, branched or unbranched and saturated or unsaturated alkyl, aryl or a heterocyclic compound. A preferred example is the nitrosylated form of isosorbide. Compounds in this group form S-nitrosothiol intermediates in vivo in the recipient human or other animal to be treated and can therefore include any structurally analogous precursor R—O—NO of the S-nitrosothiols described above.

Another group of such adducts are nitrates which donate, transfer or release nitric oxide and are selected from the group consisting of compounds that include at least one at least one $O_2N$—O—, $O_2N$—N—, $O_2N$—S— or $O_2N$—C— group. Preferred among these are those selected from the group consisting of $O_2N$—O—, $O_2N$—N—, $O_2N$—S— or $O_2N$—C-polypeptides; $O_2N$—O—, $O_2N$—N—, $O_2N$—S— or $O_2N$—C-amino acids; $O_2N$—O—, $O_2N$—N— $O_2N$—S—• or $O_2N$—C-sugars; $O_2N$—O—, $O_2N$—N—, $O_2N$—S— or $O_2N$—C-modified and unmodified oligonucleotides; $O_2N$—O—, $O_2N$—N—, $O_2N$—S— or $O_2N$—C-hydrocarbons which can be branched or unbranched, saturated or unsaturated aliphatic hydrocarbons or aromatic hydrocarbons; $O_2N$—O—, $O_2N$—N—, $O_2N$—S— or $O_2N$—C-hydrocarbons having one or more substituent groups in addition to the $O_2N$—O—, $O_2N$—N—, $O_2N$—S— or $O_2N$—C-group; and $O_2N$—O—, $O_2N$—N—, $O_2N$—S— or $O_2N$—C-heterocyclic compounds. Preferred examples are isosorbide dinitrate and isosorbide mononitrate.

Another group of such NO adducts is the nitroso-metal compounds which have the structure $(R)_u$-A-M-$(NO)_v$. R includes polypeptides (the term "polypeptide" includes proteins and also polyamino acids that do not possess an ascertained biological function, and derivatives thereof); amino acids (including natural and synthetic amino acids and their stereoisomers and racemic mixtures and derivatives thereof); sugars; modified and unmodified oligonucleotides (preferably of at least 5, and more particularly 5–200, nucleotides); and a hydrocarbon where the hydrocarbon can be a branched or unbranched, and saturated or unsaturated aliphatic hydrocarbon, or an aromatic hydrocarbon; hydrocarbons having one or more substituent groups in addition to the A-nitroso group; and heterocyclic compounds. A is S, O, or N, u and v are each integers independently selected from 1, 2 and 3, and M is a metal, preferably a transition metal. Preferred metals include iron, copper, manganese, cobalt, selenium and luthidium. Also contemplated are N-nitrosylated metal centers such as nitroprusside.

Another group of such adducts are 2-hydroxy-2-nitrosohydrazines which donate, transfer or release nitric oxide and have a $R_{61}R_{62}$-N(O-M$^+$)—NO group wherein $R_{61}$ and $R_{62}$ include polypeptides, amino acids, sugars, modified and unmodified oligonucleotides, hydrocarbons where the hydrocarbon can be a branched or unbranched, and saturated or unsaturated aliphatic hydrocarbon or an aromatic hydrocarbon, hydrocarbons having one or more substituent groups and heterocyclic compounds. M$^+$ is a metal cation, such as, for example, a Group I metal cation.

Another group of such adducts are thionitrates which donate, transfer or release nitric oxide and have the structure $R_{61}$-S—$NO_2$ wherein $R_{61}$ is as described above.

Compounds that stimulate endogenous synthesis of NO or EDRF in vivo include L-arginine, the substrate for nitric oxide synthase, cytokines, adenosine, bradykinin, calreticulin, bisacodyl, phenolphthalein, and endothelin.

When administered in vivo, the nitric oxide may be administered in combination with pharmaceutical carriers and in dosages described herein.

The nitrosated or nitrosylated compounds of the invention are used at dose ranges and over a course of dose regimen and are administered in the same or substantially equivalent vehicles/carrier by the same or substantially equivalent oral or nasal inhalant devices as their non-nitrosated or non-nitrosylated counterparts. The nitrosated or nitrosylated compounds of the invention can also be used in lower doses and in less extensive regimens of treatment. The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

While the compounds of the invention can be administered as the sole active pharmaceutical agent, they can also be used in combination with one or more compounds which are known to be effective against the specific disease state targeted for treatment. The compositions of the invention can also be administered as described above or can be made to include one or more additional active compounds which are known to be effective against the specific disease state is targeted for treatment.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

These and other aspects of the present invention will be apparent to those skilled in the art from the teachings herein.

What is claimed is:

1. A nitrosated and/or nitrosylated phosphodiesterase inhibitor having the structure:

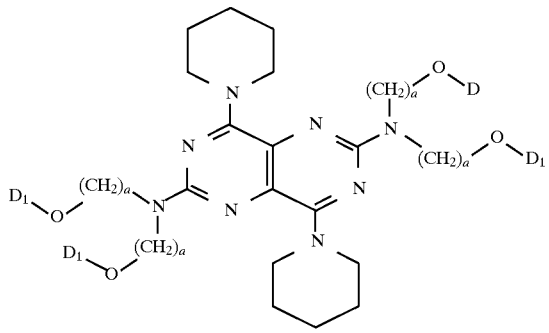

wherein a is an integer from 2 to 3

D is selected from (i) —NO; (ii) —NO$_2$; (iii) —C(R$_d$)—O—C(O)—Y—Z—[C(R$_e$)(R$_f$)]$_p$—T—Q in which R$_d$ is hydrogen, lower alkyl, cycloalkyl, aryl, alkylaryl, aryl or heteroaryl, Y is oxygen, sulfur, carbon, or NR$_i$ in which R$_i$ is hydrogen, lower alkyl, R$_e$ and R$_f$ are independently selected from hydrogen, lower alkyl, cycloalkyl, aryl, heteroaryl, arylalkyl, amino, alkylamino, amido, alkylamido, dialkylamino, carboxy or carboxamido, or taken together are carbonyl, cycloalkyl or bridged cycloalkyl, p is an integer from 1 to 6, T is a covalent bond, oxygen, sulfur or nitrogen, Z is selected from a covalent bond, alkyl, cycloalkyl, aryl, heteroaryl, arylalkyl or arylheterocyclic ring, and Q is selected from —NO or —NO$_2$; (iv) —C(O)—T$^1$—Z—[C(R$_e$)(R$_f$)]$_p$—T$^2$—Q wherein T$^1$ and T$^2$ are independently selected from T; (v) —C(O)—Z—[G—[C(R$_e$)(R$_f$)]$_p$—T—Q]$_p$ wherein G is (i) a covalent bond; (ii) —T—C(O)—; (iii) —C(O)—T, or (iv) Y; and D$_1$ is selected from D or hydrogen.

2. A composition comprising a therapeutically effective amount of the phosphodiesterase inhibitor of claim 1 and one to ten fold molar excess of a compound that donates, transfers or releases nitrogen monoxide as a charged species selected from the group consisting of nitrosonium (NO$^+$) and nitroxyl (NO$^-$), or as the neutral species, nitric oxide (NO•) or induces the production of endogenous EDRF and a pharmaceutically acceptable carrier.

3. A method for treating male impotence in humans which comprises administering to an individual in need thereof a therapeutically effective amount of a nitrosated or nitrosylated PDE inhibitor of claim 1.

4. A method for treating male impotence in humans which comprises administering to an individual in need thereof a composition comprising a therapeutically effective amount of a PDE inhibitor of claim 1 moiety, and a compound that donates, transfers or releases nitric oxide as a charged species selected from the group consisting of nitrosonium (NO$^+$) and nitroxyl (NO$^-$), or as the neutral species, nitric oxide (NO•) or stimulates endogenous production of NO or induces the production of EDRF in vivo.

* * * * *